United States Patent
Roth et al.

(10) Patent No.: US 11,590,171 B2
(45) Date of Patent: **\*Feb. 28, 2023**

(54) TARGETED REPLACEMENT OF ENDOGENOUS T CELL RECEPTORS

(71) Applicant: THE REGENTS OF THE UNIVERSITY OF CALIFORNIA, Oakland, CA (US)

(72) Inventors: Theodore Lee Roth, San Francisco, CA (US); Eric Shifrut, San Francisco, CA (US); Alexander Marson, San Francisco, CA (US); Cristina Puig Saus, Los Angeles, CA (US); Antoni Ribas, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/725,478

(22) Filed: Apr. 20, 2022

(65) Prior Publication Data

US 2022/0241336 A1 Aug. 4, 2022

Related U.S. Application Data

(63) Continuation of application No. 17/390,673, filed on Jul. 30, 2021, now Pat. No. 11,331,346, which is a continuation of application No. 17/200,301, filed on Mar. 12, 2021, now Pat. No. 11,083,753, which is a continuation of application No. 16/568,116, filed on Sep. 11, 2019, now Pat. No. 11,033,584, which is a continuation of application No. PCT/US2018/058026, filed on Oct. 29, 2018.

(60) Provisional application No. 62/578,153, filed on Oct. 27, 2017.

(51) Int. Cl.
| | |
|---|---|
| *A61K 35/17* | (2015.01) |
| *C07K 14/725* | (2006.01) |
| *C12N 9/22* | (2006.01) |
| *C12N 15/113* | (2010.01) |
| *C12N 15/85* | (2006.01) |
| *C12N 15/90* | (2006.01) |

(52) U.S. Cl.
CPC .......... *A61K 35/17* (2013.01); *C07K 14/7051* (2013.01); *C12N 9/22* (2013.01); *C12N 15/113* (2013.01); *C12N 15/85* (2013.01); *C12N 15/907* (2013.01); *C12N 2310/20* (2017.05)

(58) Field of Classification Search
CPC .................................................. A61K 35/17
See application file for complete search history.

(56) References Cited

U.S. PATENT DOCUMENTS

| | | |
|---|---|---|
| 6,824,978 B1 | 11/2004 | Cox, III et al. |
| 8,133,733 B2 | 3/2012 | Khan |
| 8,586,363 B2 | 11/2013 | Voytas et al. |
| 8,795,965 B2 | 8/2014 | Zhang |
| 9,221,886 B2 | 12/2015 | Liu et al. |
| 9,512,446 B1 | 12/2016 | Joung et al. |
| 9,526,784 B2 | 12/2016 | Liu et al. |
| 9,758,775 B2 | 9/2017 | Voytas et al. |
| 9,855,297 B2 | 1/2018 | Duchateau et al. |
| 9,890,393 B2 | 2/2018 | Duchateau et al. |
| 11,033,584 B2 | 6/2021 | Roth et al. |
| 11,083,753 B1 | 8/2021 | Roth et al. |
| 2002/0064802 A1 | 5/2002 | Raschke et al. |
| 2002/0160940 A1 | 10/2002 | Case et al. |
| 2003/0087817 A1 | 5/2003 | Cox, III et al. |
| 2003/0232410 A1 | 12/2003 | Liljedahl et al. |
| 2005/0136040 A1 | 6/2005 | Hart et al. |
| 2006/0182736 A1 | 8/2006 | Kim et al. |
| 2007/0254291 A1 | 11/2007 | Cui et al. |
| 2009/0082250 A1 | 3/2009 | Hart et al. |
| 2010/0093617 A1 | 4/2010 | Barrangou et al. |
| 2011/0145940 A1 | 6/2011 | Voytas et al. |
| 2011/0158957 A1 | 6/2011 | Bonini et al. |
| 2011/0265198 A1 | 10/2011 | Gregory et al. |
| 2012/0077270 A1 | 3/2012 | Hart et al. |
| 2012/0110685 A1 | 5/2012 | Bonas et al. |
| 2013/0236504 A1 | 9/2013 | Alexis et al. |
| 2014/0068797 A1 | 3/2014 | Doudna et al. |
| 2014/0189896 A1 | 7/2014 | Zhang et al. |
| 2014/0199767 A1 | 7/2014 | Barrangou et al. |
| 2014/0294773 A1 | 10/2014 | Brouns et al. |
| 2014/0301990 A1 | 10/2014 | Gregory et al. |
| 2014/0349402 A1 | 11/2014 | Cooper et al. |

(Continued)

FOREIGN PATENT DOCUMENTS

| | | |
|---|---|---|
| CN | 105452483 A | 3/2016 |
| WO | 0041566 A1 | 7/2000 |

(Continued)

OTHER PUBLICATIONS

Sharpe et al. (2015, Disease, Models and Mechanisms, vol. 8, pp. 337-350) (Year: 2015).*

(Continued)

*Primary Examiner* — Ram R Shukla
*Assistant Examiner* — David A Montanari
(74) *Attorney, Agent, or Firm* — Kilpatrick Townsend & Stockton LLP

(57) ABSTRACT

Provided herein are methods and compositions for editing the genome of a human T cell. In some embodiments, a heterologous T cell receptor (TCR)-β chain and a heterologous TCR-α chain are inserted into exon 1 of a TCR subunit constant gene in the genome of the T cell.

16 Claims, 23 Drawing Sheets

(56) References Cited

U.S. PATENT DOCUMENTS

| | | |
|---|---|---|
| 2014/0357530 A1 | 12/2014 | Zhang et al. |
| 2015/0016954 A1 | 1/2015 | Thibodeau et al. |
| 2015/0071903 A1 | 3/2015 | Liu et al. |
| 2015/0110762 A1 | 4/2015 | Holmes et al. |
| 2015/0164954 A1 | 6/2015 | Bonini et al. |
| 2015/0259704 A1 | 9/2015 | Church et al. |
| 2015/0283265 A1 | 10/2015 | Peyman |
| 2015/0322457 A1 | 11/2015 | Kim et al. |
| 2015/0344912 A1 | 12/2015 | Kim et al. |
| 2016/0017366 A1 | 1/2016 | Chen et al. |
| 2016/0024524 A1 | 1/2016 | Joung et al. |
| 2016/0053274 A1 | 2/2016 | D'Halluin |
| 2016/0102322 A1 | 4/2016 | Ravinder et al. |
| 2016/0160210 A1 | 6/2016 | Mali et al. |
| 2016/0200779 A1 | 7/2016 | Liu et al. |
| 2016/0264999 A1 | 9/2016 | Rao et al. |
| 2016/0298134 A1 | 10/2016 | Chen et al. |
| 2016/0298135 A1 | 10/2016 | Chen et al. |
| 2016/0298138 A1 | 10/2016 | Chen et al. |
| 2016/0304893 A1 | 10/2016 | Daboussi et al. |
| 2017/0000743 A1 | 1/2017 | Ghoroghchian et al. |
| 2017/0016027 A1 | 1/2017 | Lee et al. |
| 2017/0044569 A9 | 2/2017 | Church et al. |
| 2017/0073705 A1 | 3/2017 | Chen et al. |
| 2017/0175128 A1 | 6/2017 | Welstead et al. |
| 2017/0191082 A1 | 7/2017 | Chen et al. |
| 2017/0211075 A1 | 7/2017 | Lee et al. |
| 2017/0290858 A1 | 10/2017 | Zhao et al. |
| 2017/0296676 A1 | 10/2017 | Stephan et al. |
| 2017/0335331 A1 | 11/2017 | Zhao et al. |
| 2018/0044700 A1 | 2/2018 | Doudna et al. |
| 2018/0161447 A1 | 6/2018 | Watson et al. |
| 2018/0312848 A1 | 11/2018 | Zhao et al. |
| 2019/0388469 A1 | 12/2019 | Marson et al. |
| 2020/0048606 A1 | 2/2020 | Marson et al. |
| 2020/0362355 A1 | 11/2020 | Roth et al. |

FOREIGN PATENT DOCUMENTS

| | | |
|---|---|---|
| WO | 0183751 A2 | 11/2001 |
| WO | 0183751 A3 | 8/2002 |
| WO | 03033701 A1 | 4/2003 |
| WO | 03080809 A2 | 10/2003 |
| WO | 2004092194 A2 | 10/2004 |
| WO | 2004108883 A2 | 12/2004 |
| WO | 2005123962 A2 | 12/2005 |
| WO | 2007025097 A2 | 3/2007 |
| WO | 2008021207 A2 | 2/2008 |
| WO | 2011059836 A2 | 5/2011 |
| WO | 2011072246 A2 | 6/2011 |
| WO | 2011139336 A1 | 11/2011 |
| WO | 2013134349 A1 | 9/2013 |
| WO | 2013176772 A1 | 11/2013 |
| WO | 2014089290 A1 | 6/2014 |
| WO | 2014093661 A2 | 6/2014 |
| WO | 2014144761 A2 | 9/2014 |
| WO | 2014153470 A2 | 9/2014 |
| WO | 2014161821 A1 | 10/2014 |
| WO | 2015035136 A2 | 3/2015 |
| WO | 2015048690 A1 | 4/2015 |
| WO | 2015057980 A1 | 4/2015 |
| WO | 2015073867 A1 | 5/2015 |
| WO | 2015086795 A1 | 6/2015 |
| WO | 2015089419 A2 | 6/2015 |
| WO | 2015089462 A1 | 6/2015 |
| WO | 2015089486 A2 | 6/2015 |
| WO | 2015115903 A1 | 8/2015 |
| WO | 2015117021 A1 | 8/2015 |
| WO | 2015089419 A9 | 11/2015 |
| WO | 2016036754 A1 | 3/2016 |
| WO | 2016044745 A1 | 3/2016 |
| WO | 2016049251 A1 | 3/2016 |
| WO | 2016057951 A2 | 4/2016 |
| WO | 2016069282 A1 | 5/2016 |
| WO | 2016097751 A1 | 6/2016 |
| WO | 2016118697 A1 | 7/2016 |
| WO | 2016123578 A1 | 8/2016 |
| WO | 2016118697 A9 | 9/2016 |
| WO | 2016135559 A2 | 9/2016 |
| WO | 2016172359 A2 | 10/2016 |
| WO | 2016196388 A1 | 12/2016 |
| WO | 2016205680 A1 | 12/2016 |
| WO | 2016205703 A1 | 12/2016 |
| WO | 2017004509 A1 | 1/2017 |
| WO | 2017011519 A1 | 1/2017 |
| WO | 2017035659 A1 | 3/2017 |
| WO | 2017044661 A1 | 3/2017 |
| WO | 2017053729 A1 | 3/2017 |
| WO | 2017058751 A1 | 4/2017 |
| WO | 2017062451 A1 | 4/2017 |
| WO | 2017070056 A1 | 4/2017 |
| WO | 2017070169 A1 | 4/2017 |
| WO | 2017070429 A1 | 4/2017 |
| WO | 2017079673 A1 | 5/2017 |
| WO | 2017091630 A1 | 6/2017 |
| WO | 2017106528 A2 | 6/2017 |
| WO | 2017115128 A2 | 7/2017 |
| WO | 2017156484 A1 | 9/2017 |
| WO | 2017177137 A1 | 10/2017 |
| WO | 2017180989 A2 | 10/2017 |
| WO | 2017181110 A1 | 10/2017 |
| WO | 2017186550 A1 | 11/2017 |
| WO | 2017189336 A1 | 11/2017 |
| WO | 2017210334 A1 | 12/2017 |
| WO | 2017220527 A1 | 12/2017 |
| WO | 2018035387 A1 | 2/2018 |
| WO | 2018039084 A1 | 3/2018 |
| WO | 2018068135 A1 | 4/2018 |
| WO | 2018073391 A1 | 4/2018 |
| WO | 2018073393 A2 | 4/2018 |
| WO | 2018094291 A1 | 5/2018 |
| WO | 2019089610 A1 | 5/2019 |

OTHER PUBLICATIONS

Baldanzi et al., "SAP-Mediated Inhibition of Diacylglycerol Kinase α Regulates TCR-Induced Diacylglycerol Signaling," The Journal of Immunology, vol. 187, No. 11, Dec. 1, 2011, pp. 5941-5951.

Chira et al., "Progresses Towards Safe and Efficient Gene Therapy Vectors," Oncotarget, vol. 6, No. 31, 2015, pp. 30675-30703.

Cornu et al., "T Refining Strategies to Translate Genome Editing to the Clinic," Nat. Med. 23, 2017, pp. 415-423.

EP18871537.9, Extended European Search Report, dated Oct. 6, 2021, 14 pages.

Eyquem et al., "Targeting a CAR to the TRAC Locus with CRISPR/Cas9 Enhances Tumour Rejection," Nature, vol. 543, No. 7643, 2017, pp. 113-117.

Foley et al., "HCV T Cell Receptor Chain Modifications to Enhance Expression, Pairing, and Antigen Recognition in T Cells for Adoptive Transfer," Molecular Therapy Oncolytics, vol. 5, Jun. 16, 2017, pp. 105-115.

Glusman et al., "Comparative Genomics of the Human and Mouse T Cell Receptor Loci," Immunity, vol. 15, No. 3, Sep. 2001, pp. 337-349.

Hornung et al., "Intracellular DNA Recognition," Nat. Rev. Immunol. 10, 2010, pp. 123-130.

Kaneko et al., "Simple Knockout by Electroporation of Engineered Endonucleases into Intact Rat Embryos," Scientific Reports vol. 4, No. 6382, Oct. 1, 2014, 5 pages.

Liang et al., "Enhanced CRISPR/Cas9-Mediated Precise Genome Editing by Improved Design and Delivery of gRNA, Cas9 Nuclease, and Donor DNA," Journal of Biotechnology, vol. 241, Jan. 10, 2017, pp. 136-146.

Mandal et al., "Efficient Ablation of Genes in Human Hematopoietic Stem and Effector Cells Using CRISPR/Cas9," Cell Stem Cell, vol. 15, No. 5, Nov. 6, 2014, 15 pages.

Okamoto et al., "A Promising Vector for TCR Gene Therapy: Differential Effect of siRNA, 2A Peptide, and Disulfide Bond on the Introduced TCR Expression," Molecular Therapy—Nucleic Acids, vol. 1, No. 12, Dec. 18, 2012, pp. 1-11.

(56) References Cited

OTHER PUBLICATIONS

PCT/US2018/058026, "International Search Report and Written Opinion," dated Jan. 17, 2019, 13 pages.
Rosenberg, "Adoptive Cell Transfer as Personalized Immunotherapy for Human Cancer," Science vol. 80, No. 348, 2015, pp. 62-68.
Roth et al., "Reprogramming Human T Cell Function and Specificity with Non-Viral Genome Targeting," bioRxiv preprint doi: htttgs://doi.org/10.: 10:/183418, Dec. 7, 2017, pp. 1-75.
Roth et al., "Reprogramming Human T Cell Function and Specificity with Non-Viral Genome Targeting," Nature, vol. 559, No. 7714, Jul. 19, 2018, pp. 405-409.
Sadelain et al., "Therapeutic T Cell Engineering," Nature 545, 2017, pp. 423-431.
Schumann et al., "Generation of Knock-In Primary Human T Cells Using Cas9 Ribonucleoproteins," Proceedings of the National Academy of Sciences, vol. 112, No. 33, 2015, pp. 10437-10442.
Verhoeven et al., "Lentiviral Vector Gene Transfer into Human T Cells," Methods Mol. Biol. vol. 506, 2009, pp. 97-114.
Zhao et al., "High-Efficiency Transfection of Primary Human and Mouse T Lymphocytes Using RNA Electroporation," Mol. Ther., vol. 13, No. 1, Jan. 2006, pp. 151-159.
U.S. Appl. No. 16/568,116, "Corrected Notice of Allowability," dated Apr. 1, 2021, 5 pages.
U.S. Appl. No. 16/568,116, "Non-Final Office Action," dated Jun. 22, 2020, 8 pages.
U.S. Appl. No. 16/568,116, "Notice of Allowance," Feb. 5, 2021, 10 pages.
PCT/US2018/058026, "International Preliminary Report on Patentability," dated May 7, 2020, 11 pages.
U.S. Appl. No. 17/200,301, Notice of Allowance, dated May 27, 2021, 6 pages.
U.S. Appl. No. 17/390,673, Non-Final Office Action, datedc Sep. 16, 2021, 11 pages.
U.S. Appl. No. 17/390,673, Notice of Allowance, dated Jan. 24, 2022, 8 pages.

\* cited by examiner

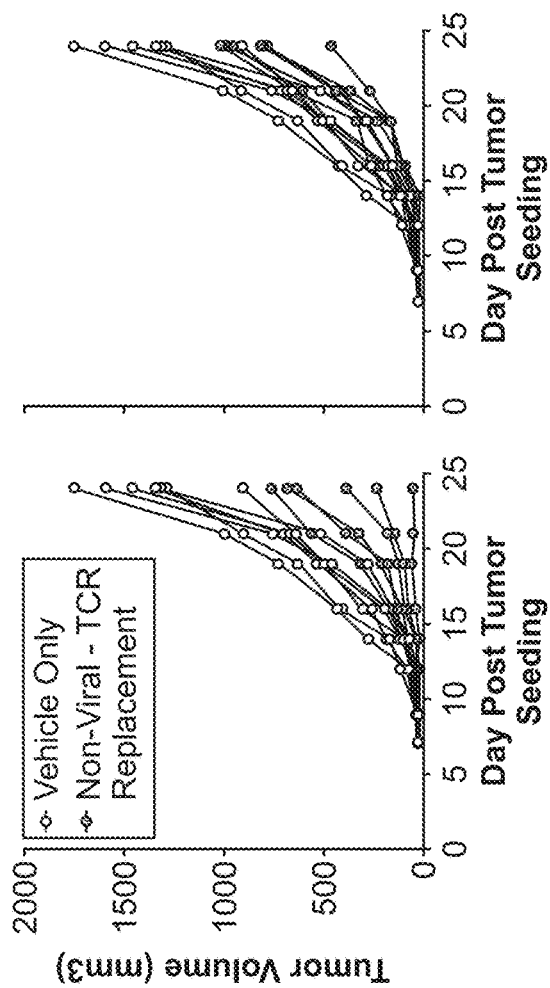
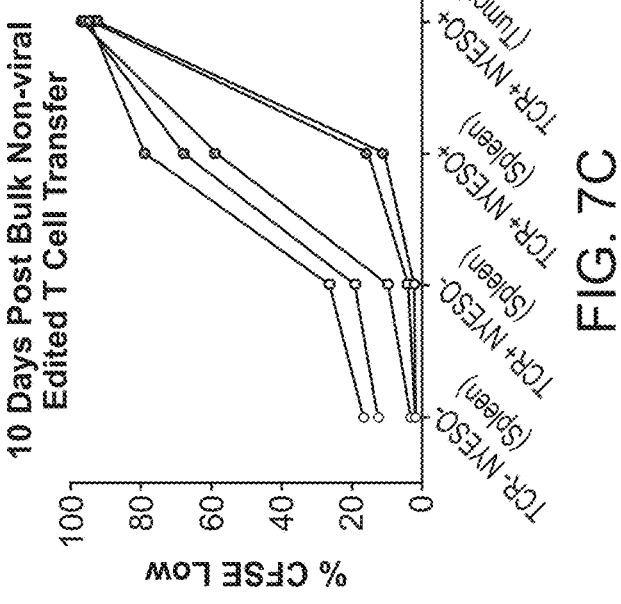
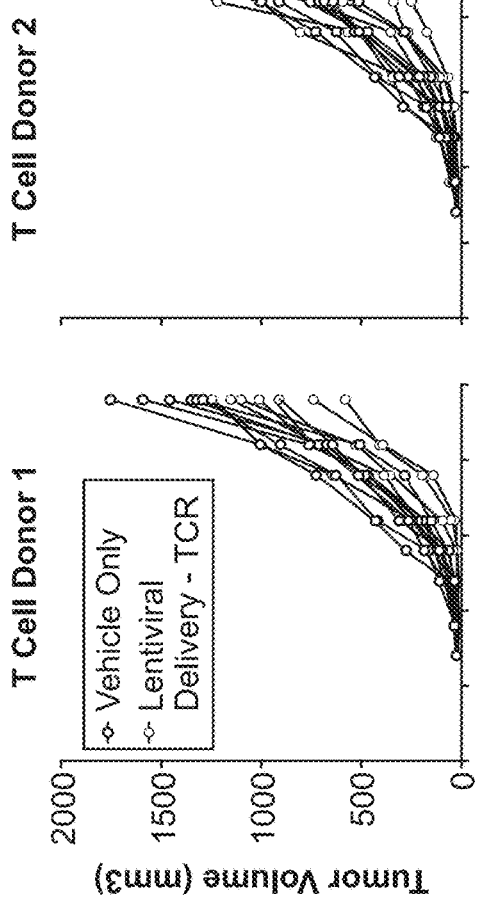
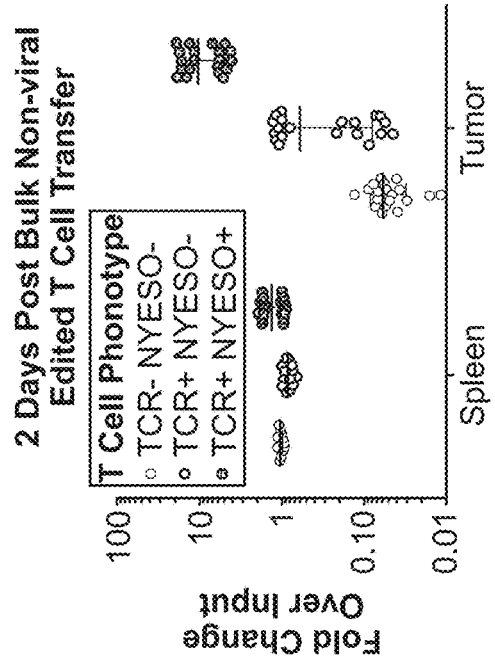
FIG. 7B
FIG. 7C
FIG. 7D

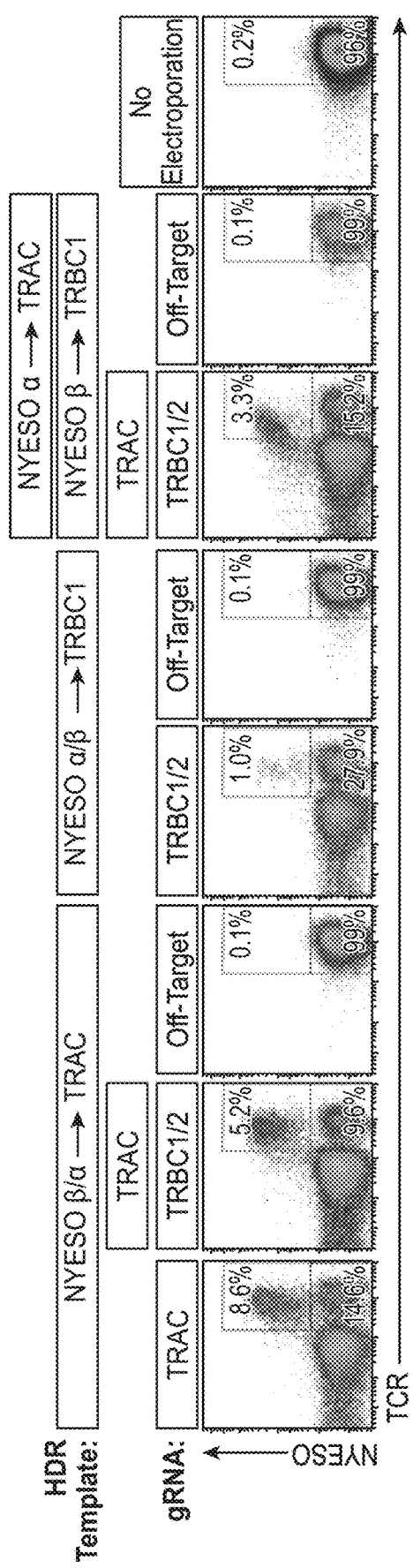
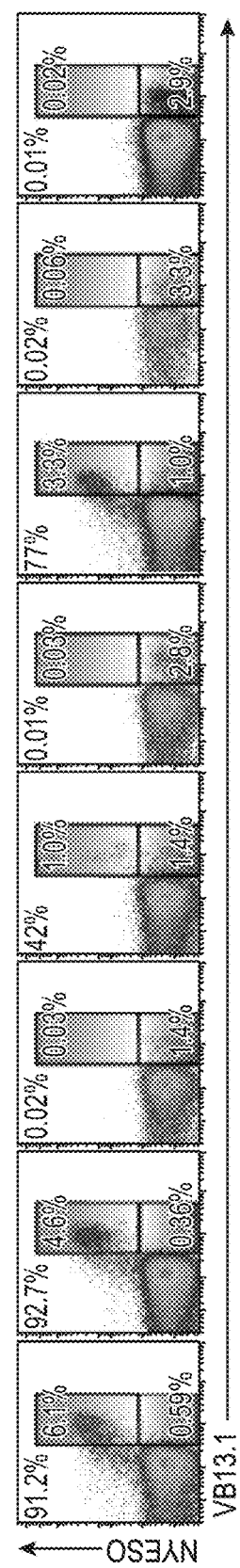
FIG. 9B
FIG. 9C

TARGETED REPLACEMENT OF ENDOGENOUS T CELL RECEPTORS

PRIOR RELATED APPLICATIONS

This application is a continuation of U.S. patent application Ser. No. 17/390,673, filed Jul. 30, 2021, which is a continuation of U.S. patent application Ser. No. 17/200,301, filed on Mar. 12, 2021, which is a continuation of U.S. patent application Ser. No. 16/568,116, filed on Sep. 11, 2019, now issued as U.S. Pat. No. 11,033,584, which is a continuation of International Patent Application No. PCT/US2018/058026, filed on Oct. 29, 2018, which claims the benefit of U.S. Provisional Application No. 62/578,153 filed on Oct. 27, 2017, each of which is incorporated by reference herein in its entirety.

BACKGROUND OF THE INVENTION

T cells are the most actively studied cell type in the growing field of adoptive cellular therapeutics. T cells interact specifically with the target of their T cell receptor (TCR), enabling highly specific responses with minimal side effects. These highly effective and specific responses can be engineered towards novel antigens and targets by inserting a new receptor with the desired specificity into a T cell. However, development of entirely new types of receptors is time consuming, expensive, and fails to take advantage of the fact that, through development of the endogenous T cell repertoire, the body naturally produces TCRs that bind almost any possible antigenic target. The ability to obtain human T cells and replace their endogenous TCR with a TCR having a desired antigen specificity could be transformative in the development and application of adoptive T cell therapies.

BRIEF SUMMARY OF THE INVENTION

The present disclosure is directed to compositions and methods for editing the genome of a human T cell. The inventors have discovered that a heterologous TCR can be inserted into a targeted region in the genome of a T cell, such that the heterologous TCR is under the control of an endogenous TCR promoter. The methods and compositions provided herein can be used to replace an endogenous TCR in a human T cell with a heterologous TCR having a desired antigen specificity. In some embodiments, the targeted region in the genome of a T cell is the native T cell receptor locus.

In some embodiments, the present disclosure provides a method of editing the genome of a human T cell. In some embodiments, the method comprises inserting into a target region in exon 1 of a T cell receptor (TCR)-subunit constant gene in the human T cell, a nucleic acid sequence encoding, from the N-terminus to the C-terminus, (i) a first self-cleaving peptide sequence; (ii) a first heterologous TCR subunit chain, wherein the TCR subunit chain comprises the variable region and the constant region of the TCR subunit; (iii) a second self-cleaving peptide sequence; (iv) a variable region of a second heterologous TCR subunit chain; and (v) a portion of the N-terminus of the endogenous TCR subunit, wherein, if the endogenous TCR subunit is a TCR-alpha (TCR-α) subunit, the first heterologous TCR subunit chain is a heterologous TCR-beta (TCR-β) subunit chain and the second heterologous TCR subunit chain is a heterologous TCR-α subunit chain, and wherein if the endogenous TCR subunit is a TCR-β subunit, the first heterologous TCR subunit chain is a heterologous TCR-α subunit chain and the second heterologous TCR subunit chain is a heterologous TCR-subunit chain. In some embodiments, the method comprises inserting into a target region in exon 1 of a TCR alpha subunit constant gene (TRAC) in the human T cell, a nucleic acid sequence encoding, from the N-terminus to the C-terminus, (i) a first self-cleaving peptide sequence; (ii) a heterologous TCR-β chain; (iii) a second self-cleaving peptide sequence; (iv) a variable region of a heterologous TCR-α chain; and (v) a portion of the N-terminus of the endogenous TCR-α subunit.

In some embodiments, the method comprises inserting into a target region in exon 1 of a TCR-beta subunit constant gene (TRBC) in the human T cell, a nucleic acid sequence encoding, from the N-terminus to the C-terminus, (i) a first self-cleaving peptide sequence; (ii) a heterologous TCR-α chain; (iii) a second self-cleaving peptide sequence; (iv) a variable region of a heterologous TCR-β chain; and (v) a portion of the N-terminus of the endogenous TCR-β subunit.

In some embodiments, the nucleic acid is inserted by introducing a viral vector comprising the nucleic acid into the T cell. In some embodiments, the nucleic is inserted by introducing a non-viral vector comprising the nucleic acid into the T cell. In some embodiments, the nucleic acid is inserted into the T cell by introducing into the T cell, (a) a targeted nuclease that cleaves a target region in exon 1 of a TCR-α subunit constant gene (TRAC) to create an insertion site in the genome of the T cell; and (b) the nucleic acid sequence, wherein the nucleic acid sequence is incorporated into the insertion site by homology directed repair (HDR). In some embodiments, the nucleic acid is inserted into the T cell by introducing into the T cell, (a) a targeted nuclease that cleaves a target region in exon 1 of a TCR-β subunit constant gene (TRBC) to create an insertion site in the genome of the T cell; and (b) the nucleic acid sequence, wherein the nucleic acid sequence is incorporated into the insertion site by homology directed repair (HDR). In some embodiments, the 5' end and the 3' end of the nucleic acid comprise nucleotide sequences that are homologous to genomic sequences flanking the target region. In some embodiments, the 5' end and the 3' end of the nucleic acid comprise nucleotide sequences that are homologous to genomic sequences flanking the insertion site. In some embodiments, the targeted nuclease introduces a double-stranded break at the insertion site. In some embodiments, the nucleic acid sequence is introduced into the cell as a double-stranded or a single-stranded nucleic acid. In some embodiments, the nucleic acid is introduced into the cell as a double-stranded or a single stranded DNA template. In some embodiments, the nucleic acid sequence is introduced into the cell as a linear nucleic acid.

In some embodiments, the first self-cleaving peptide and the second self-cleaving peptide are the same or different viral 2A peptides.

In some embodiments, the targeted nuclease is selected from the group consisting of an RNA-guided nuclease domain, a transcription activator-like effector nuclease (TALEN), a zinc finger nuclease (ZFN) and a megaTAL. In some embodiments, the RNA-guided nuclease is a Cpf1 nuclease or a Cas9 nuclease, and the method further comprises introducing into the cell a guide RNA that specifically hybridizes to the target region in exon 1 of the TRAC. In some embodiments, the Cpf1 nuclease or the Cas9 nuclease, the guide RNA and the nucleic acid are introduced into the cell as a ribonucleoprotein complex (RNP)-DNA template complex, wherein the RNP-DNA template complex comprises: (i) the RNP, wherein the RNP comprises the Cpf1 nuclease or the Cas9 nuclease, and the guide RNA; and (ii) the DNA template.

In some embodiments, the molar ratio of RNP to DNA template in the complex is from about 3:1 to about 100:1. In some embodiments, the RNP-DNA template complex is formed by incubating the RNP with the DNA template for about ten to about thirty minutes, at a temperature of about 20° to 25° C. In some embodiments, the RNP-DNA template complex and the cell are mixed prior to introducing the RNP-DNA template complex into the cell. In some embodiments, the RNP-DNA template complex comprises at least two structurally different RNP complexes. In some embodiments, the at least two structurally different RNP complexes contain structurally different guide RNAs. In some embodiments, each of the structurally different RNP complexes comprises a Cas9 nickase, and wherein the structurally different guide RNAs hybridize to opposite strands of the target region.

In some embodiments, the introducing comprises electroporation. In some embodiments, the nucleic acid is introduced into a population of about $1 \times 10^5$ to about $2 \times 10^6$ T cells. In some examples, the targeted nuclease and the DNA template are introduced into a population of about $1 \times 10^5$ to about $2 \times 10^6$ T cells. In some embodiments, at least two structurally different DNA templates are introduced into the cells. In some embodiments, the at least two structurally-different DNA templates are non-viral templates. In some embodiments, each of the at least two structurally different DNA templates encodes a unique combination of a variable region of a heterologous TCR-β chain of an antigen specific T cell receptor and a variable region of a heterologous TCR-α chain of an antigen specific T cell receptor. In some embodiments, the T cell is a regulatory T cell, an effector T cell, or a naïve T cell. In some embodiments, the T cell is an effector T cell, and wherein the effector T cell is a CD8$^+$ T cell. In some embodiments, the T cell is an effector T cell, and wherein the effector T cell is a CD4$^+$ T cell. In some embodiments, the effector T cell is a CD4$^+$CD8$^+$ T cell.

In some embodiments, the method further comprises culturing the T cells under conditions that allow expression of the heterologous TCR-β chain and the heterologous TCR-α chain to form an antigen-specific T cell receptor. In some embodiments, the method further comprises culturing the modified T cells under conditions effective for expanding the population of modified cells. In some embodiments, the method further comprises purifying T cells that express the antigen-specific T cell receptor.

In some embodiments, the present disclosure provides a method of editing the genome of a human T cell comprising: (a) inserting into a target region in exon 1 of a TCR alpha subunit constant gene (TRAC) in the human T cell a first nucleic acid sequence encoding, from the N-terminus to the C-terminus, (i) a self-cleaving peptide sequence; (ii) a heterologous TCR-α chain of an antigen specific T cell receptor; and (iii) a portion of the N-terminus of exon 1 of the endogenous TCR alpha subunit; and (b) inserting into a target region in exon 1 of a TCR beta subunit constant gene (TRBC) in the human T cell a second nucleic acid sequence encoding, from the N-terminus to the C-terminus a second nucleic acid sequence encoding sequence encoding, from the N-terminus to the C-terminus, (i) a second self-cleaving peptide sequence; (ii) a heterologous TCR-0 chain of an antigen specific T cell receptor; and (iii) a portion of the N-terminus of exon 1 of the endogenous TCR beta subunit.

In some embodiments, the first and/or second nucleic acid sequence are inserted by introducing a viral vector comprising the first and/or second nucleic acid to the T cell. In some embodiments, the first and/or second nucleic acid sequence are inserted by introducing a non-viral vector comprising the first and/or second nucleic acid to the T cell. In some embodiments, the first and second nucleic acids are inserted into the T cell by introducing (a) one or more targeted nucleases that create a first insertion site in exon 1 of a TRAC and a second insertion site in exon 1 of a TCR beta subunit constant gene (TRBC); and (b) the first nucleic acid sequence; and (c) the second nucleic acid sequence, wherein the first nucleic acid sequence is inserted into the first insertion site in exon 1 of the TRAC and the second nucleic acid sequence is inserted into the second insertion site in exon 1 of the TRBC by homology directed repair (HDR). In some embodiments, the nucleic acid sequence is introduced into the cell as a double-stranded or a single-stranded DNA template. In some embodiments, the nucleic acid sequence is introduced into the cell as a linear DNA template.

In some embodiments, the 5' end and the 3' end of the first nucleic acid sequence comprise nucleotide sequences that are homologous to genomic sequences flanking the target region in exon 1 of the TRAC gene. In some embodiments, the 5' end and the 3' end of the first nucleic acid sequence comprise nucleotide sequences that are homologous to genomic sequences flanking the first insertion site in exon 1 of the TRAC gene. In some embodiments, the 5' end and the 3' end of the second nucleic acid sequence comprise nucleotide sequences that are homologous to genomic sequences flanking the target region in exon 1 of the TRBC gene. In some embodiments, the 5' end and the 3' end of the second nucleic acid sequence comprise nucleotide sequences that are homologous to genomic sequences flanking the second insertion in exon 1 of the TRBC gene.

In some embodiments, the one or more targeted nucleases introduce a double-stranded break at the first and second insertion sites. In some embodiments, the first self-cleaving peptide and the second self-cleaving peptide are the same or different viral 2A peptides. In some embodiments, the one or more targeted nucleases are selected from the group consisting of an RNA-guided nuclease domain, a transcription activator-like effector nuclease (TALEN), a zinc finger nuclease (ZFN) or a megaTAL.

In some embodiments, the RNA-guided nuclease is a Cpf1 nuclease or a Cas9 nuclease and wherein the method further comprises introducing into the cell a first guide RNA that specifically hybridizes to a target region in exon 1 of the TRAC, and a second guide RNA that specifically hybridizes to a target region in exon 1 of the TRBC. In some embodiments, the Cpf1 nuclease or the Cas9 nuclease, the first guide RNA and the first nucleic acid are introduced into the cell as a ribonucleoprotein complex (RNP)-DNA template complex, wherein the RNP-DNA template complex comprises: (i) the RNP, wherein the RNP comprises the Cpf1 nuclease or the Cas9 nuclease, and the first guide RNA; and (ii) the first DNA template. In some embodiments, the Cpf1 nuclease or the Cas9 nuclease, the second guide RNA, and the second nucleic acid are introduced into the cell as a RNP-DNA template complex, wherein the RNP-DNA template complex comprises: (i) the RNP, wherein the RNP comprises a Cpf1 nuclease or Cas9 nuclease, and the second guide RNA; and (ii) the second DNA template.

In some embodiments, the molar ratio of RNP to DNA template in the complex is from about 3:1 to about 100:1. In some embodiments, the RNP-DNA template complex is formed by incubating the RNP with the DNA template for about ten to about thirty minutes, at a temperature of about 20° to 25° C. In some embodiments, the RNP-DNA template complex comprises at least two structurally different RNP complexes. In some embodiments, each of the structurally different RNP complexes comprises a Cas9 nickase, and wherein the structurally different guide RNAs hybridize to opposite strands of the target region. In some embodiments, the introducing comprises electroporation.

In some embodiments, the first and second nucleic acids are introduced into about $1\times10^5$ to about $2\times10^6$ T cells. In some embodiments, one or more targeted nucleases and the first and second nucleic acids are introduced into about $1\times10^5$ to about $2\times10^6$ T cells. In some embodiments, at least two structurally different first DNA templates are introduced into the cells. In some embodiments, the at least two structurally different first DNA templates comprise different variable regions of a TCR-α chain of an antigen specific T cell receptor. In some embodiments, at least two structurally different second DNA templates are introduced into the cells. In some embodiments, the at least two structurally different second DNA templates comprise different variable regions of a TCR-β chain of an antigen specific T cell receptor.

In some embodiments, the T cell is a regulatory T cell, an effector T cell, or a naïve T cell. In some embodiments, the T cell is an effector T cell, wherein the effector T cell is a CD8+ T cell. In some embodiments, the T cell is an effector T cell, wherein the effector T cell is a CD4+ T cell. In some embodiments, the effector T cell is a CD4+CD8+ T cell.

In some embodiments, the method further comprises culturing the T cells under conditions that allow expression of the heterologous TCR-β chain and the heterologous TCR-α chain to form an antigen-specific T cell receptor. In some embodiments, the method further comprises culturing the T cells under conditions that allow expression of the heterologous TCR-β chain and the heterologous TCR-α chain to form an antigen-specific T cell receptor. In some embodiments, the method further comprises culturing the modified T cells under conditions effective for expanding the population of modified cells. In some embodiments, the method further comprises purifying T cells that express the antigen-specific T cell receptor.

In other embodiments, the present disclosure provides a modified T cell comprising a nucleic acid sequence encoding, from the N-terminus to the C-terminus, (i) a first self-cleaving peptide sequence; (ii) a variable region of a heterologous T cell receptor (TCR)-β chain; (iii) a second self-cleaving peptide sequence; (iv) a variable region of a heterologous TCR-α chain; and (v) a portion of the N-terminus of the endogenous TCR alpha subunit, wherein the nucleic acid sequence is integrated into exon 1 of the TRAC gene.

In some embodiments, the present disclosure further provides a modified T cell comprising: a) a first nucleic acid sequence encoding, from N-terminus to C-terminus, (i) a first self-cleaving sequence, (ii) the variable region of a heterologous TCR-α chain, and (iii) a portion of the N-terminus of the endogenous TCR-α chain; and b) a second nucleic acid sequence encoding, from N-terminus to C-terminus, (i) a first self-cleaving sequence, (ii) the variable region of a heterologous TCR-β chain, and (iii) a portion of the N-terminus of the endogenous TCR-β chain, wherein the first nucleic acid sequence is integrated into exon 1 of the TRAC gene and the second nucleic sequence is integrated into exon 1 of the TRBC gene.

In some embodiments, the present disclosure further provides a method of treating cancer in a human subject comprising: a) obtaining T cells from the subject; b) modifying the T cells to express a heterologous antigen-specific T cell receptor, wherein the T cell receptor recognizes a tumor-specific antigen in the subject; and c) administering the modified T cells to the subject.

Using the methods and compositions described herein for modifying T cells to express a heterologous TCR-α chain and a heterologous TCR-β chain, one can also edit a human gamma delta (γδ) T cell. For example, in some embodiments, the method comprises inserting into a target region in exon 1 of a T cell receptor gamma subunit constant (TRGC) gene in the human T cell, a nucleic acid sequence encoding, from the N-terminus to the C-terminus, (i) a first self-cleaving peptide sequence; (ii) a variable region of a heterologous TCR-β chain; (iii) a second self-cleaving peptide sequence; (iv) a variable region of a heterologous TCR-α chain; and (v) a portion of the N-terminus of the endogenous TCR-α.

In other embodiments, the method comprises inserting into a target region in exon 1 of a T cell receptor gamma subunit constant (TRGC) gene in the human T cell, a nucleic acid sequence encoding, from the N-terminus to the C-terminus, (i) a first self-cleaving peptide sequence; (ii) a variable region of a heterologous TCR-β chain; (iii) a second self-cleaving peptide sequence; (iv) a full length heterologous TCR-α chain; and (v) a stop codon, such that, upon insertion of the nucleic acid, the nucleic acids encoding the heterologous TCR-β and TCR-α sequences are under the control of the endogenous TCR-γ promoter.

In other embodiments, the method comprises inserting into a target region in exon 1 of a T cell receptor gamma subunit constant (TRGC) gene in the human T cell, a nucleic acid sequence encoding, from the N-terminus to the C-terminus, (i) a first self-cleaving peptide sequence; (ii) a variable region of a heterologous TCR-δ chain; (iii) a second self-cleaving peptide sequence; (iv) a variable region of a heterologous TCR-γ chain; and (v) a portion of the N-terminus of the endogenous TCR-γ subunit. Also provided is a method of editing the genome of a human T cell, comprising inserting into a target region in exon 1 of a TRAC gene in the human T cell, a nucleic acid sequence encoding, from the N-terminus to the C-terminus, (i) a first self-cleaving peptide sequence; (ii) a variable region of a heterologous TCR-γ chain; (iii) a second self-cleaving peptide sequence; (iv) a variable region of a heterologous TCR-δ chain; and (v) a portion of the N-terminus of the endogenous TCR-α subunit. In other embodiments, the method comprises inserting into a target region in exon 1 of a T cell receptor gamma subunit constant (TRAC) gene in the human T cell, a nucleic acid sequence encoding, from the N-terminus to the C-terminus, (i) a first self-cleaving peptide sequence; (ii) a variable region of a heterologous TCR-γ chain; (iii) a second self-cleaving peptide sequence; (iv) a full-length heterologous TCR-δ chain; and (v) a stop codon, such that upon insertion, of the nucleic acid, the heterologous TCR-γ and TCR-δ sequences are under the control of the endogenous TCR-α promoter.

BRIEF DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIGS. 7A-7F show the in vivo functionality of T cells with non-viral TCR replacement. (A) Diagram of in vivo human antigen specific tumour xenograft model. (B) Two days following transfer of $5\times10^6$ bulk non-virally targeted T cells (~10% TCR+NYESO-1+, ~10% TCR+NYESO-1-, and ~80% TCR− NYESO-1-), NY-ESO-1+ non-virally edited T cells preferentially accumulated in the tumour vs. the spleen. n=5 mice for each of four human T cell donors. (C) Ten days following transfer of $5\times10^6$ bulk non-virally targeted CFSE labeled T cells, NYESO-1 TCR+ cells showed greater proliferation than TCR− or TCR+NYESO-1− T cells, and showed greater proliferation (CFSE Low) in the tumour than in the spleen. At ten days post transfer TCR− and TCR+NYESO− T cells were difficult to find in the tumour. (D) Individual longitudinal tumour volume tracks for data summarized in FIG. 8F. (E,F) In these experiments, seventeen days following T cell transfer (D), non-virally TCR replaced cells appeared to show greater NY-ESO-1 TCR expression and lower expression of exhaustion markers. Transfer of both lentivirally transduced and non-viral TCR replaced cells showed significant reductions in tumour burden on day 24. In this experimental model, non-viral TCR replacement showed further reductions compared to the lentiviral transduction (FIG. 8F).

FIGS. 9B-9C show TCR replacement by targeting an entire new TCR into TRAC (FIG. 9B, also possible with a multiplexed knockout of TCR-β), an entire new TCR into TRBC1/2 (FIG. 9C), or multiplexed replacement with a new TCR-α into TRAC and a new TCR-β into TRBC1/2.

DEFINITIONS

Figure 1A:
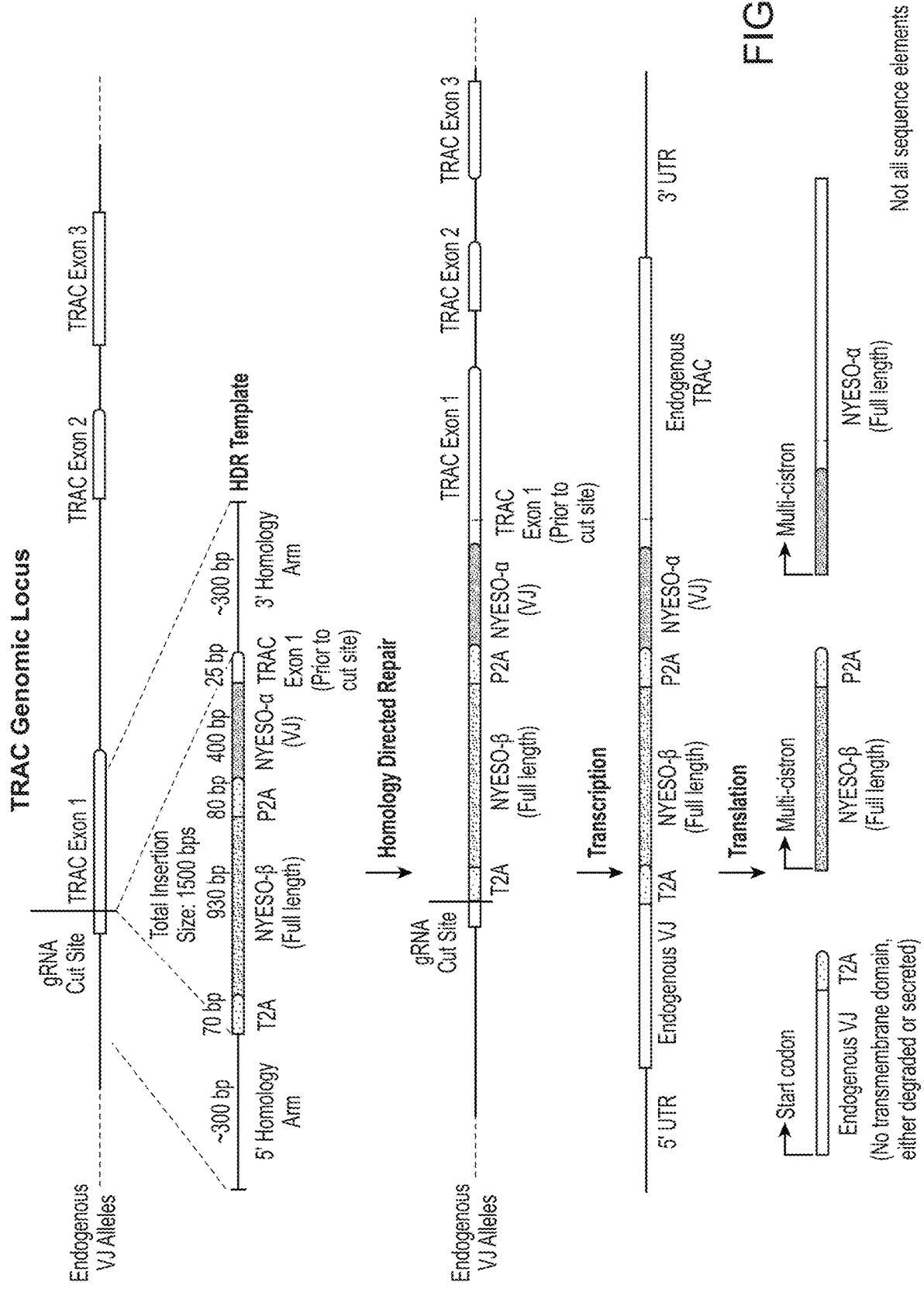
FIG. 1A is a schematic depicting insertion of a single non-viral DNA template comprising a nucleic acid sequence encoding, from the N-terminus to the C-terminus, (i) a T2A self-cleaving peptide sequence; (ii) a full-length (i.e., variable region and constant region) of a heterologous TCR-β chain (NYESO-β); (iii) a P2A self-cleaving peptide sequence; (iv) a variable region of a heterologous TCR-α chain (NYESO-α); and (v) a portion of the N-terminus of the endogenous TCR alpha subunit into a T cell via homology directed repair. After insertion of the DNA template in exon 1 of the TRAC gene via homology directed repair, the DNA template was transcribed and translated to produce a full-length NYESO-β chain and a full-length NYESO-α chain that forms an antigen-specific TCR that recognizes the NY-ESO-1 melanoma neoantigen.

As used in this specification and the appended claims, the singular forms "a," "an," and "the" include plural reference unless the context clearly dictates otherwise.

The term "nucleic acid" or "nucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The term "gene" can refer to the segment of DNA involved in producing or encoding a polypeptide chain. It may include regions preceding and following the coding region (leader and trailer) as well as intervening sequences (introns) between individual coding segments (exons). Alternatively, the term "gene" can refer to the segment of DNA involved in producing or encoding a non-translated RNA, such as an rRNA, tRNA, guide RNA (e.g., a single guide RNA), or micro RNA "Treating" refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating.

A "promoter" is defined as one or more a nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

"Polypeptide," "peptide," and "protein" are used interchangeably herein to refer to a polymer of amino acid residues. As used herein, the terms encompass amino acid chains of any length, including full-length proteins, wherein the amino acid residues are linked by covalent peptide bonds.

As used herein, the term "complementary" or "complementarity" refers to specific base pairing between nucleotides or nucleic acids. In some embodiments, for example, and not to be limiting, base pairing between a guide RNA and a target region in exon 1 of the TRAC gene is described. Complementary nucleotides are, generally, A and T (or A and U), and G and C. The guide RNAs described herein can comprise sequences, for example, DNA targeting sequence that are perfectly complementary or substantially complementary (e.g., having 1-4 mismatches) to a genomic sequence in exon 1 of the TRAC gene in a T cell.

As used throughout, by subject is meant an individual. For example, the subject is a mammal, such as a primate, and, more specifically, a human. The term does not denote a particular age or sex. Thus, adult and newborn subjects, whether male or female, are intended to be covered. As used herein, patient or subject may be used interchangeably and can refer to a subject afflicted with a disease or disorder.

The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize an RNA-mediated nuclease, for example, Cas9, in complex with guide and activating RNA to recognize and cleave foreign nucleic acid. Guide RNAs having the activity of both a guide RNA and an activating RNA are also known in the art. In some cases, such dual activity guide RNAs are referred to as a single guide RNA (sgRNA).

Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chlroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9; 497(7448):254-7; and Jinek, et al., Science. 2012 Aug. 17; 337(6096):816-21. Variants of Any of the Cas9 nucleases provided herein can be optimized for efficient activity or enhanced stability in the host cell. Thus, engineered Cas9 nucleases are also contemplated.

As used herein, the term "Cas9" refers to an RNA-mediated nuclease (e.g., of bacterial or archeal orgin, or derived therefrom). Exemplary RNA-mediated nucleases include the foregoing Cas9 proteins and homologs thereof. Other RNA-mediated nucleases include Cpf1 (See, e.g., Zetsche et al., Cell, Volume 163, Issue 3, p 759-7'71, 22 Oct. 2015) and homologs thereof. Similarly, as used herein, the term "Cas9 ribonucleoprotein" complex and the like refers to a complex between the Cas9 protein, and a crRNA (e.g., guide RNA or single guide RNA), the Cas9 protein and a trans-activating crRNA (tracrRNA), the Cas9 protein and a guide RNA, or a combination thereof (e.g., a complex containing the Cas9 protein, a tracrRNA, and a crRNA guide RNA). It is understood that in any of the embodiments described herein, a Cas9 nuclease can be subsitututed with a Cpf1 nuclease.

As used herein, the phrase "editing" in the context of editing of a genome of a cell refers to inducing a structural change in the sequence of the genome at a target genomic region. For example, the editing can take the form of inserting a nucleotide sequence into the genome of the cell. The nucleotide sequence can encode a polypeptide or a fragment thereof. Such editing can be performed, for example, by inducing a double stranded break within a target genomic region, or a pair of single stranded nicks on opposite strands and flanking the target genomic region. Methods for inducing single or double stranded breaks at or within a target genomic region include the use of a Cas9 nuclease domain, or a derivative thereof, and a guide RNA, or pair of guide RNAs, directed to the target genomic region.

As used herein, the phrase "introducing" in the context of introducing a nucleic acid or a complex comprising a nucleic acid, for example, an RNP-DNA template complex, refers to the translocation of the nucleic acid sequence or the RNP-DNA template complex from outside a cell to inside the cell. In some cases, introducing refers to translocation of the nucleic acid or the complex from outside the cell to inside the nucleus of the cell. Various methods of such translocation are contemplated, including but not limited to, electroporation, contact with nanowires or nanotubes, receptor mediated internalization, translocation via cell penetrating peptides, liposome mediated translocation, and the like.

As used herein the phrase "heterologous" refers to a nucleic acid sequence or a polypeptide not naturally found in a human T cell. The term "heterologous sequence" refers to a sequence not normally found in a given T cell in nature. As such, a heterologous nucleotide or protein sequence may be: (a) foreign to its host cell (i.e., is exogenous to the cell); (b) naturally found in the host cell (i.e., endogenous) but present at an unnatural quantity in the cell (i.e., greater or lesser quantity than naturally found in the host cell); or (c) be naturally found in the host cell but positioned outside of its natural locus.

As used herein, the phrase "primary" in the context of a primary cell is a cell that has not been transformed or immortalized. Such primary cells can be cultured, sub-cultured, or passaged a limited number of times (e.g., cultured 0, 1, 2, 3, 4, 5, 6, 7, 8, 9, 10, 11, 12, 13, 14, 15, 16, 17, 18, 19, or 20 times). In some cases, the primary cells are adapted to in vitro culture conditions. In some cases, the primary cells are isolated from an organism, system, organ, or tissue, optionally sorted, and utilized directly without culturing or sub-culturing. In some cases, the primary cells are stimulated, activated, or differentiated. For example, primary T cells can be activated by contact with (e.g., culturing in the presence of) CD3, CD28 agonists, IL-2, IFN-γ, or a combination thereof.

As used herein, the phrase "T cell" refers to a lymphoid cell that expresses a T cell receptor molecule. T tells include human alpha beta (αβ) T cells and human gamma delta (γδ) T cells. T cells include, but are not limited to, naïve T cells, stimulated T cells, primary T cells (e.g., uncultured), cultured T cells, immortalized T cells, helper T cells, cytotoxic T cells, memory T cells, regulatory T cells, natural killer T cells, combinations thereof, or sub-populations thereof. T cells can be CD4$^+$, CD8$^+$, or CD4$^+$ and CD8$^+$. T cells can be helper cells, for example helper cells of type T$_H$1, T$_H$2, T$_H$3, T$_H$9, T$_H$17, or T$_{FH}$. T cells can be cytotoxic T cells. Regulatory T cells can be FOXP3$^+$ or FOXP3". T cells can be alpha/beta T cells or gamma/delta T cells. In some cases, the T cell is a CD4$^+$CD25$^{hi}$CD127$^{lo}$ regulatory T cell. In some cases, the T cell is a regulatory T cell selected from the group consisting of type 1 regulatory (Tr1), T$_H$3, CD8+ CD28-, Treg17, and Qa-1 restricted T cells, or a combination or sub-population thereof. In some cases, the T cell is a FOXP3$^+$ T cell. In some cases, the T cell is a CD4$^+$ CD25$^{lo}$CD127$^{hi}$ effector T cell. In some cases, the T cell is a CD4$^+$CD25$^{lo}$CD127$^{hi}$CD45RA$^{hi}$CD45RO$^-$ naïve T cell. A T cell can be a recombinant T cell that has been genetically manipulated. In some cases, the recombinant T cell has a recombinant (e.g., heterologous) T cell receptor.

As used herein, the term "TCR receptor" is a heterodimer consisting of two TCR subunit chains, (e.g. TCR-α and TCR-β, TCRγ and TCRδ) that functions in activation of T cells in response to an antigen. When expressed in a T cell, each TCR subunit chain of the TCR receptor contains a constant region that anchors the TCR subunit chain to the cell membrane and a variable region that functions in antigen recognition and binding, for example, when a first TCR subunit chain (e.g., TCR-α) and a second TCR subunit chain (e.g., TCR-β) chain form a heterodimeric TCR receptor.

As used herein, the term "non-homologous end joining" or NHEJ refers to a cellular process in which cut or nicked ends of a DNA strand are directly ligated without the need for a homologous template nucleic acid. NHEJ can lead to the addition, the deletion, substitution, or a combination thereof, of one or more nucleotides at the repair site.

As used herein, the term "homology directed repair" or HDR refers to a cellular process in which cut or nicked ends of a DNA strand are repaired by polymerization from a homologous template nucleic acid. Thus, the original sequence is replaced with the sequence of the template. The homologous template nucleic acid can be provided by homologous sequences elsewhere in the genome (sister chromatids, homologous chromosomes, or repeated regions on the same or different chromosomes). Alternatively, an exogenous template nucleic acid can be introduced to obtain a specific HDR-induced change of the sequence at the target site. In this way, specific mutations can be introduced at the cut site.

As used herein, a single-stranded DNA template or a double-stranded DNA template refers to a DNA oligonucleotide that can be used by a cell as a template for editing the genome of T call, for example, by HDR. Generally, the single-stranded DNA template or a double-stranded DNA template has at least one region of homology to a target site. In some cases, the single-stranded DNA template or double-stranded DNA template has two homologous regions, for example, a 5' end and a 3' end, flanking a region that contains a heterologous sequence to be inserted at a target cut or insertion site.

DETAILED DESCRIPTION OF THE INVENTION

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art; therefore, information well known to the skilled artisan is not necessarily included.

Provided herein are compositions and methods for editing the genome of a human T cell. The inventors have discovered that a heterologous TCR can be inserted into a targeted region in the genome of a T cell, such that the heterologous TCR is under the control of an endogenous TCR promoter. The methods and compositions provided herein can be used to make modified T cells having a desired antigen specificity. These modified T cells can be used, for example, to treat cancer, autoimmune disease or infection in a subject.

In some embodiments, a nucleic acid sequence encoding a variable region of a heterologous TCR-β chain and a variable region of a heterologous TCR-α chain is inserted into exon 1 of the TRAC gene in the genome of the T cell. In some embodiments, a nucleic acid sequence encoding a variable region of a heterologous TCR-α chain and a variable region of a heterologous TCR-β chain is inserted into exon 1 of the TRBC gene, for example, into exon 1 of TRBC1 or TRBC2, in the genome of the T cell. In some embodiments, the nucleic acid sequence is introduced via homology directed repair or as otherwise described herein.

In some embodiments, (a) a first nucleic acid sequence encoding a variable region of a heterologous TCR-α chain of a T cell receptor; and (b) a second nucleic acid sequence encoding a variable region of a heterologous TCR-β chain of an antigen specific T cell receptor are inserted into exon 1 of the TRAC gene and exon 1 of the TRBC gene, respectively. In some embodiments, the nucleic acid sequence is introduced via homology directed repair or as otherwise described herein.

Methods of Making Modified Human T Cells

Methods for editing the genome of a T cell include a method of editing the genome of a human T cell comprising inserting a nucleic acid sequence or construct into a target region in exon 1 of a T cell receptor (TCR)-subunit constant gene in the human T cell. The nucleic acid construct encodes sequentially, from the N-terminus to the C-terminus a first heterologous TCR subunit chain, wherein the TCR subunit chain comprises the variable region and the constant region of the TCR subunit chain, and a variable region of a second heterologous TCR subunit chain. The construct further encodes a first self-cleaving peptide that precedes the variable region of the first heterologous TCR subunit chain, and a second self-cleaving peptide between the first heterologous TCR subunit chain and the second heterologous TCR subunit chain. In some methods, if the endogenous TCR subunit is a TCR-alpha (TCR-α) subunit, the first heterologous TCR subunit chain is a heterologous TCR-beta (TCR-β) subunit chain and the second heterologous TCR subunit chain is a heterologous TCR-α subunit chain. In some methods, if the endogenous TCR subunit is a TCR-β subunit, the first heterologous TCR subunit chain is a heterologous TCR-α subunit chain and the second heterologous TCR subunit chain is a heterologous TCR-β subunit chain.

In some embodiments, the nucleic acid construct or sequence encoding a variable region of a TCR subunit chain is a nucleic acid construct or sequence encoding the TCR subunit chain, i.e., a nucleic acid encoding the variable region and the constant region of the TCR subunit chain, e.g., a full-length TCR subunit chain. In some examples, the nucleic acid encodes a full-length TCR-α, TCR-β, TCR-γ, or TCR-δ subunit chain. In some examples, the nucleic acid construct or sequence encodes a first heterologous, TCR subunit chain (e.g., full-length TCR subunit chain) and a variable region of a second heterologous TCR subunit chain. In some examples, the first and second heterologous TCR subunit chains are different. In some examples, the nucleic acid construct encodes, from the N-terminus to the C-terminus, a heterologous, full-length TCR-β subunit chain and a variable region of a heterologous TCR-α subunit chain. In other examples, the nucleic acid construct encodes, from the N-terminus to the C-terminus, a heterologous, full-length TCR-α subunit chain and a variable region of a heterologous TCR-β subunit chain.

Methods for editing the genome of a T cell include a method of editing the genome of a human T cell comprise inserting a nucleic acid sequence or construct into a target region in exon 1 of the TCR-α subunit (TRAC) gene in the human T cell. In some embodiments, the target region is in exon 1 of the constant domain of TRAC gene. In other embodiments, the target region is in exon 1, exon 2 or exon 3, prior to the start of the sequence encoding the TCR-α transmembrane domain. The nucleic acid construct encodes sequentially, from the N-terminus to the C-terminus, a variable region of a heterologous T cell receptor (TCR)-β chain, followed by a variable region of a heterologous TCR-α chain. The construct further encodes a first self-cleaving peptide that precedes the variable region of a heterologous TCR-β chain, and a second self-cleaving peptide between the variable region of the heterologous TCR-β chain and the variable region of the heterologous TCR-α chain. The construct further encodes a portion of the N-terminus of the endogenous TCR-α subunit after the variable region of the heterologous TCR-α chain. Depending on the insertion site in the TRAC gene, the size of the nucleic acid encoding the N-terminal portion of the endogenous TCR-α subunit can vary. The size of the nucleic acid encoding the N-terminal portion of the endogenous TCR-α subunit will depend on the number of nucleotides in the endogenous TRAC nucleic acid sequence between the start of TRAC exon 1 and the targeted insertion site. See, for example, FIG. 1A, where 25 nucleotides encoding the N-terminus of the endogenous TCR-α subunit were included in the construct because the number of nucleotides between the start of TRAC exon 1 and the insertion site was 25 nucleotides. Similarly, if the number of nucleotides between the start of TRAC exon 1 and the insertion site is between less than or greater than 25 nucleotides, a nucleic acid of less than or greater than 25 nucleotides encoding the N-terminal portion of the endogenous TCR-α subunit can be in the construct. In some examples, the nucleic acid construct encodes, from the N-terminus to the C-terminus, a first self-cleaving peptide sequence, a heterologous (i.e., variable region and constant region) TCR-β subunit chain (e.g., a full-length TCR-β subunit chain), a second self-cleaving peptide sequence, a variable region of a heterologous TCR-α subunit chain and a portion of the N-terminus of the endogenous TCR-α subunit. Exemplary constructs include those set forth in FIG. 1A.

Methods for editing the genome of a T cell also include a method of editing the genome of a human T cell comprise inserting a nucleic acid sequence or construct into a target region in exon 1 of a TCR-β subunit (TRBC) gene in the human T cell. In some embodiments, the target region is in exon 1 of the TRBC1 or TRBC2 gene. The nucleic acid construct encodes sequentially, from the N-terminus to the C-terminus, a variable region of a heterologous T cell receptor (TCR)-α chain, followed by a variable region of a heterologous TCR-β chain. The construct further encodes a first self-cleaving peptide that precedes the variable region of a heterologous TCR-α chain, and a second self-cleaving peptide between the variable region of the heterologous TCR-α chain and the variable region of the heterologous TCR-β chain. The construct further encodes a portion of the N-terminus of the endogenous TCR-β subunit after the variable region of the heterologous TCR-β chain. Depending on the insertion site in TRBC1 or TRBC2, the size of the nucleic acid encoding the N-terminal portion of the endogenous TCR-β subunit can vary. The size of the nucleic acid encoding the N-terminal portion of the endogenous TCR-α subunit will depend on the number of nucleotides in the endogenous TRBC nucleic acid sequence between the start of exon1 of TRBC1 or TRBC2 TRBC and the targeted insertion site. See, for example, FIG. 1B, where 25 nucleotides encoding the N-terminus of the endogenous TCR-β subunit were included in the construct because the number of nucleotides between the start of TRBC exon 1 and the insertion site was 25 nucleotides. Similarly, if the number of nucleotides between the start of TRBC1 or TRBC2 exon 1 and the insertion site is between less than or greater than 25 nucleotides, a nucleic acid of less than or greater than 25 nucleotides encoding the N-terminal portion of the endogenous TCR-β subunit can be in the construct. In some examples, the nucleic acid construct encodes, from the N-terminus to the C-terminus, a first-self-cleaving peptide, a heterologous (i.e., variable region and constant region) TCR-α subunit chain (e.g., a full-length TCR-α subunit chain), a second self-cleaving peptide, a variable region of a heterologous TCR-β subunit chain and a portion of the N-terminus of the endogenous TCR-β subunit. Exemplary constructs include those set forth in FIG. 1B.

Examples of self-cleaving peptides include, but are not limited to, self-cleaving viral 2A peptides, for example, a porcine teschovirus-1 (P2A) peptide, a Thosea asigna virus (T2A) peptide, an equine rhinitis A virus (E2A) peptide, or a foot-and-mouth disease virus (F2A) peptide. Self-cleaving 2A peptides allow expression of multiple gene products from a single construct. (See, for example, Chng et al. "Cleavage efficient 2A peptides for high level monoclonal antibody expression in CHO cells," MAbs 7(2): 403-412 (2015)). In some embodiments, the first and second self-cleaving peptides are the same. In other embodiments, the first and second self-cleaving peptides are different.

Upon insertion, the construct encoding the first self-cleaving peptide, the heterologous full-length TCR-β chain, the second self-cleaving peptide, the variable region of the TCR-α chain, and the portion of the N-terminus of the endogenous TCR-α subunit, in that order, is under the control of the endogenous TCR-α promoter and TCR-α regulatory elements. Once the construct is incorporated into the genome of the T cell and under the control of the endogenous TCR-α promoter, the T cells can be cultured under conditions that allow transcription of the inserted construct into a single mRNA sequence encoding a fusion polypeptide. The fusion polypeptide comprises the first self-cleaving peptide, the heterologous full-length TCR-β chain, the second self-cleaving peptide, the heterologous full-length TCR-α chain, and the portion of the N-terminus of the endogenous TCR-α subunit, in that order.

Similarly, upon insertion in TRBC1 or TRBC2, the construct encoding the first self-cleaving peptide, the heterologous full-length TCR-α chain, the second self-cleaving peptide, the variable region of the TCR-β chain, and the portion of the N-terminus of the endogenous TCR-β subunit, in that order, is under the control of the endogenous TCR-β promoter and TCR-β regulatory elements. Once the construct is incorporated into the genome of the T cell and under the control of the endogenous TCR-β promoter, the T cells can be cultured under conditions that allow transcription of the inserted construct into a single mRNA sequence encoding a fusion polypeptide. The fusion polypeptide comprises the first self-cleaving peptide, the heterologous full-length TCR-α chain, the second self-cleaving peptide, the heterologous full-length TCR-β chain, and the portion of the N-terminus of the endogenous TCR-β subunit, in that order.

By inserting the construct into exon 1 of the TRAC gene, the remaining exons of the TRAC gene (exons 2 and 3) are spliced together with exon 1 into the final mRNA sequence. Translation of this mRNA sequence results in expression of one protein that self-cleaves into three, separate polypeptide sequences, i.e., an inactive, endogenous variable region peptide lacking a transmembrane domain, (which can be, e.g., degraded in the endoplasmic reticulum or secreted following translation), a full-length heterologous antigen-specific TCR-β chain, and a full length heterologous antigen-specific TCR-α chain (See FIG. 1A). The full-length antigen specific TCR-β chain and the full length antigen-specific TCR-α chain form a TCR with desired antigen-specificity.

Similarly, by inserting the construct into exon 1 of the TRBC1/2 gene, the remaining exons of the TRBC1/2 gene (exons 2-4) are spliced together with exon 1 into the final mRNA sequence. Translation of this mRNA sequence results in expression of one protein that self-cleaves into three, separate polypeptide sequences, i.e., an inactive, endogenous variable region peptide lacking a transmembrane domain, (which can be, e.g., degraded in the endoplasmic reticulum or secreted following translation), a full-length heterologous antigen-specific TCR-β chain, and a full length heterologous antigen-specific TCR-α chain. The full-length antigen specific TCR-β chain and the full length antigen-specific TCR-α chain form a TCR with desired antigen-specificity.

Alternatively, a heterologous TCR-α chain coding sequence, for example, a sequence encoding the variable region of a TCR-α chain and a heterologous TCR-β chain coding sequence, for example, a sequence encoding the variable region of a TCR-β chain are inserted into the genome of a T cell, wherein the heterologous TCR-α chain is inserted in exon 1 of the TRAC gene and the heterologous TCR-β chain is inserted into exon 1 of the TRBC gene. In some embodiments, a first nucleic acid sequence or construct encoding a heterologous TCR-α chain and second nucleic acid sequence or construct encoding a heterologous TCR-β chain are used to insert the heterologous TCR-α chain in exon 1 of the TRAC gene and the heterologous TCR-β chain in exon 1 of the TRBC gene, respectively.

In methods that use a first and second nucleic acid construct, the target region for insertion of the nucleic acid encoding a heterologous TCR-α chain is in exon 1 of the TRAC gene. In some embodiments, the target region for insertion of the nucleic acid encoding a heterologous TCR-β chain is downstream of the endogenous TRBC1 or TRBC2 promoter and located in exon 1 of the TRBC1 or TRBC 2 gene. The first nucleic acid encodes sequentially, from the N-terminus to the C-terminus, a first self-cleaving peptide, followed by heterologous TCR-α chain, followed by a portion of the N-terminus of the endogenous TCR-α subunit. The second nucleic acid construct encodes sequentially, from the N-terminus to the C-terminus, a second self-cleaving peptide, followed by a nucleic acid encoding a heterologous TCR-β chain, followed by a portion of the N-terminus of the endogenous TCR-β subunit. Exemplary constructs include those set forth in FIG. 2.

Upon insertion, the first construct encoding the first self-cleaving peptide and the heterologous TCR-α chain, in that order, is under the control of the endogenous TCR-α promoter and TCR-α regulatory elements. The second construct encoding the second self-cleaving peptide and the heterologous TCR-β chain, in that order, is under the control of the endogenous TCR-β promoter and TCR-β regulatory elements. Once the constructs are incorporated into the genome of the T cell and under the control of the endogenous TCRα and TCR-β promoters, the T cells are cultured under conditions that allow transcription of the first construct and the second construct into separate mRNA sequences. By inserting the first construct in exon 1 of the TRAC gene, the remaining exons of the TRAC gene (exons 2 and 3) are spliced together with exon 1 into a final mRNA sequence encoding the full-length heterologous TCR-α chain. Similarly, by inserting the second construct in exon 1 of the TRBC gene, the remaining exons of the TRBC gene (exons 2 and 3) are spliced together with exon 1 into a mRNA sequence encoding the full-length heterologous TCR-β chain.

Translation of the mRNA sequence encoding the first self-cleaving peptide and the full-length heterologous TCR-α chain results in expression of an inactive, endogenous variable region peptide lacking a transmembrane domain (which can be, e.g., degraded in the endoplasmic reticulum or secreted following translation), and a full-length heterologous antigen-specific TCR-α chain. Translation of the mRNA sequence encoding the second self-cleaving peptide and the full-length heterologous TCR-β chain results in expression of an inactive, endogenous variable region peptide lacking a transmembrane domain (which can be, e.g., degraded in the endoplasmic reticulum or secreted following translation), and a full-length heterologous antigen-specific TCR-β chain. The full-length heterologous, antigen specific TCR-β chain and the full-length heterologous, antigen-specific TCR-α chain form a TCR with desired antigen-specificity.

In the methods provided herein, the variable region of a heterologous TCR-β chain comprises variable (V), diversity (D) and joining (J) alleles. In the methods provided herein, the variable region of a heterologous TCR-α chain comprises V and J alleles. See, for example, Kuby, J., *Immunology*, 7th Ed., W.H. Freeman & Co., New York (2013).

In some embodiments, the nucleic acid sequence is inserted into the genome of the T cell by introducing a vector, for example, a viral vector, comprising the nucleic acid. Examples of viral vectors include, but are not limited to, adeno-associated viral (AAV) vectors, retroviral vectors or lentiviral vectors. In some embodiments, the lentiviral vector is an integrase-deficient lentiviral vector.

In some embodiments, the nucleic acid sequence is inserted into the genome of the T cell via non-viral delivery. In non-viral delivery methods, the nucleic acid can be naked DNA, or in a non-viral plasmid or vector.

In some embodiments, the nucleic acid is inserted into the T cell by introducing into the T cell, (a) a targeted nuclease that cleaves a target region in exon 1 of a TRAC gene to create an insertion site in the genome of the T cell; and (b) the nucleic acid sequence, wherein the nucleic acid sequence is incorporated into the insertion site by HDR. In some embodiments, the nucleic acid is inserted into the T cell by introducing into the T cell, (a) a targeted nuclease that cleaves a target region in exon 1 of a TRBC gene to create an insertion site in the genome of the T cell; and (b) the nucleic acid sequence, wherein the nucleic acid sequence is incorporated into the insertion site by HDR.

In some embodiments, the method further comprises introducing into the cell a guide RNA that specifically hybridizes to the target region of exon 1 of the TRAC gene. In some embodiments, the method further comprises introducing into the cell a guide RNA that specifically hybridizes to the target region of exon 1 of the TRBC gene.

In embodiments that use first and second nucleic acid sequences to insert the heterologous TCR-α chain and the heterologous TCR-β chain into exon 1 of the TRAC gene and exon 1 of the TRBC gene, respectively, the first and second nucleic acids are inserted into the T cell by introducing into the T cell, (a) one or more targeted nucleases that create a first insertion site in exon 1 of the TRAC gene and a second insertion site in exon 1 of the TRBC gene; (b) the first nucleic acid sequence; and (c) the second nucleic acid sequence. In some embodiments, the method further comprises introducing into the cell a guide RNA that specifically hybridizes to the target region of exon 1 of the TRAC gene and a guide RNA that specifically hybridizes to the target region of exon 1 of the TRBC gene.

In some embodiments, each of the 5' and the 3' ends of the nucleic acid sequence comprise nucleotide sequences that are homologous to genomic sequences flanking a target region in the genome of a T cell, for example, a target region in exon 1 of the TRAC gene or a target region in exon 1 of the TRBC gene. In some cases, a nucleotide sequence that is homologous to a genomic sequence is about 50 to 300 nucleotides in length. In some cases, a nucleotide sequence that is homologous to a genomic sequence, or a portion thereof, is at least 80%, 90%, 95%, complementary to the genomic sequence. In some embodiments, the 5' and 3' ends of the nucleic acid sequence comprise nucleotide sequences that are homologous to genomic sequences at an insertion site in exon 1 of the TRAC gene. In some embodiments, the 5' and 3' ends of the nucleic acid sequence comprise nucleotide sequences that are homologous to genomic sequences flanking an insertion site in exon 1 of a TRBC gene.

In some cases, the nucleic acid sequence is introduced into the cell as a linear DNA template. In some cases, the nucleic acid sequence is introduced into the cell as a double-stranded DNA template. In some cases, the DNA template is a single-stranded DNA template. In some cases, the single-stranded DNA template is a pure single-stranded DNA template. As used herein, by "pure single-stranded DNA" is meant single-stranded DNA that substantially lacks the other or opposite strand of DNA. By "substantially lacks" is meant that the pure single-stranded DNA lacks at least 100-fold more of one strand than another strand of DNA. In some cases, the DNA template is a double-stranded or single-stranded plasmid or mini-circle.

In some embodiments, the targeted nuclease is selected from the group consisting of an RNA-guided nuclease domain, a transcription activator-like effector nuclease (TALEN), a zinc finger nuclease (ZFN) and a megaTAL (See, for example, Merkert and Martin "Site-Specific Genome Engineering in Human Pluripotent Stem Cells," Int. J. Mol. Sci. 18(7): 1000 (2016)). In some embodiments, the RNA-guided nuclease is a Cas9 nuclease and the method further comprises introducing into the cell a guide RNA that specifically hybridizes to a target region in the genome of the T cell, for example, a target region in exon 1 of the TRAC gene. In other embodiments, the RNA-guided nuclease is a Cas9 nuclease and the method further comprises introducing into the cell a guide RNA that specifically hybridizes to a target region in exon 1 of the TRBC gene.

As used throughout, a guide RNA (gRNA) sequence is a sequence that interacts with a site-specific or targeted nuclease and specifically binds to or hybridizes to a target nucleic acid within the genome of a cell, such that the gRNA and the targeted nuclease co-localize to the target nucleic acid in the genome of the cell. Each gRNA includes a DNA targeting sequence or protospacer sequence of about 10 to 50 nucleotides in length that specifically binds to or hybridizes to a target DNA sequence in the genome. For example, the DNA targeting sequence is about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the gRNA comprises a crRNA sequence and a transactivating crRNA (tracrRNA) sequence. In some embodiments, the gRNA does not comprise a tracrRNA sequence.

Generally, the DNA targeting sequence is designed to complement (e.g., perfectly complement) or substantially complement the target DNA sequence. In some cases, the DNA targeting sequence can incorporate wobble or degenerate bases to bind multiple genetic elements. In some cases, the 19 nucleotides at the 3' or 5' end of the binding region are perfectly complementary to the target genetic element or elements. In some cases, the binding region can be altered to increase stability. For example, non-natural nucleotides, can be incorporated to increase RNA resistance to degradation. In some cases, the binding region can be altered or designed to avoid or reduce secondary structure formation in the binding region. In some cases, the binding region can be designed to optimize G-C content. In some cases, G-C content is preferably between about 40% and about 60% (e.g., 40%, 45%, 50%, 55%, 60%). In some embodiments, the Cas9 protein can be in an active endonuclease form, such that when bound to target nucleic acid as part of a complex with a guide RNA or part of a complex with a DNA template, a double strand break is introduced into the target nucleic acid. In the methods provided herein, a Cas9 polypeptide or a nucleic acid encoding a Cas9 polypeptide can be introduced into the T cell. The double strand break can be repaired by HDR to insert the DNA template into the genome of the T cell. Various Cas9 nucleases can be utilized in the methods described herein. For example, a Cas9 nuclease that requires an NGG protospacer adjacent motif (PAM) immediately 3' of the region targeted by the guide RNA can be utilized. Such Cas9 nucleases can be targeted to a region in exon 1 of the TRAC or exon 1 of the TRBC that contains an NGG sequence. As another example, Cas9 proteins with orthogonal PAM motif requirements can be used to target sequences that do not have an adjacent NGG PAM sequence. Exemplary Cas9 proteins with orthogonal PAM sequence specificities include, but are not limited to those described in Esvelt et al., Nature Methods 10: 1116-1121 (2013).

In some cases, the Cas9 protein is a nickase, such that when bound to target nucleic acid as part of a complex with a guide RNA, a single strand break or nick is introduced into the target nucleic acid. A pair of Cas9 nickases, each bound to a structurally different guide RNA, can be targeted to two proximal sites of a target genomic region and thus introduce a pair of proximal single stranded breaks into the target genomic region, for example exon 1 of a TRAC gene or exon 1 of a TRBC gene. Nickase pairs can provide enhanced specificity because off-target effects are likely to result in single nicks, which are generally repaired without lesion by base-excision repair mechanisms. Exemplary Cas9 nickases include Cas9 nucleases having a D10A or H840A mutation (See, for example, Ran et al. "Double nicking by RNA-guided CRISPR Cas9 for enhanced genome editing specificity," *Cell* 154(6): 1380-1389 (2013)).

In some embodiments, the Cas9 nuclease, the guide RNA and the nucleic acid sequence are introduced into the cell as a ribonucleoprotein complex (RNP)-DNA template complex, wherein the RNP-DNA template complex comprises: (i) the RNP, wherein the RNP comprises the Cas9 nuclease and the guide RNA; and (ii) the DNA template encoding a heterologous TCR-β chain and a heterologous TCR-α chain, wherein the DNA template is inserted into exon 1 of the TRAC gene via HDR. In some embodiments, the Cas9 nuclease, the guide RNA and the nucleic acid sequence are introduced into the cell as a ribonucleoprotein complex (RNP)-DNA template complex, wherein the RNP-DNA template complex comprises: (i) the RNP, wherein the RNP comprises the Cas9 nuclease and the guide RNA; and (ii) the DNA template encoding a heterologous TCR-β chain and a heterologous TCR-α chain, wherein the DNA template is inserted into exon 1 of the TRBC gene via HDR.

In some embodiments, where separate constructs are used to insert a heterologous TCR-α chain into exon 1 of the TRAC gene in a T cell, and a heterologous TCR-β chain into exon 1 of the TRBC gene in a T cell, (a) a first (RNP)-DNA template complex, wherein the first RNP-DNA template complex comprises: (i) a first RNP, wherein the RNP comprises the Cas9 nuclease and a first guide RNA that specifically hybridizes to a target region in exon 1 of the TRAC gene; and (ii) a DNA template encoding a heterologous TCR α subunit; and (b) a second (RNP)-DNA template complex, wherein the second RNP-DNA template complex comprises: (i) a second RNP, wherein the second RNP comprises the Cas9 nuclease and second guide RNA that specifically hybridizes to a target region in exon 1 of the TRBC gene; and (ii) a DNA template encoding a heterologous TCR β subunit are introduced into the cell. In some embodiments, the Cas9 nuclease in the first RNP-DNA template complex and the Cas9 nuclease in the second RNP-DNA template complex are the same. In some embodiments, the Cas9 nuclease in the first RNP-DNA template complex and the Cas9 nuclease in the second RNP-DNA template complex are different.

In some embodiments, the molar ratio of RNP to DNA template can be from about 3:1 to about 100:1. For example, the molar ratio can be from about 5:1 to 10:1, from about 5:1 to about 15:1, 5:1 to about 20:1; 5:1 to about 25:1; from about 8:1 to about 12:1; from about 8:1 to about 15:1, from about 8:1 to about 20:1, or from about 8:1 to about 25:1.

In some embodiments, the DNA template in the RNP-DNA template complex is at a concentration of about 2.5 pM to about 25 pM. In some embodiments, the amount of DNA template is about 1 µg to about 10 µg.

In some cases, the RNP-DNA template complex is formed by incubating the RNP with the DNA template for less than about one minute to about thirty minutes, at a temperature of about 20° C. to about 25° C. In some embodiments, the RNP-DNA template complex and the cell are mixed prior to introducing the RNP-DNA template complex into the cell.

In some embodiments the nucleic acid sequence or the RNP-DNA template complex is introduced into the T cells by electroporation. Methods, compositions, and devices for electroporating cells to introduce a RNP-DNA template complex can include those described in the examples herein. Additional or alternative methods, compositions, and devices for electroporating cells to introduce a RNP-DNA template complex can include those described in WO/2006/001614 or Kim, J. A. et al. Biosens. Bioelectron. 23, 1353-1360 (2008). Additional or alternative methods, compositions, and devices for electroporating cells to introduce a RNP-DNA template complex can include those described in U.S. Patent Appl. Pub. Nos. 2006/0094095; 2005/0064596; or 2006/0087522. Additional or alternative methods, compositions, and devices for electroporating cells to introduce a RNP-DNA template complex can include those described in Li, L. H. et al. Cancer Res. Treat. 1, 341-350 (2002); U.S. Pat. Nos. 6,773,669; 7,186,559; 7,771,984; 7,991,559; 6,485,961; 7,029,916; and U.S. Patent Appl. Pub. Nos: 2014/0017213; and 2012/0088842. Additional or alternative methods, compositions, and devices for electroporating cells to introduce a RNP-DNA template complex can include those described in Geng, T. et al. J. Control Release 144, 91-100 (2010); and Wang, J., et al. Lab. Chip 10, 2057-2061 (2010).

In some embodiments, a plurality of RNP-DNA template complexes comprising at least two structurally different RNP-DNA template complexes are introduced into a cell. A As used throughout, the phrase "plurality" means two or more. In some embodiments, the at least two structurally different RNP-DNA template complexes contain structurally different guide RNAs. In some embodiments, wherein the at least two structurally different RNP complexes contain structurally different guide RNAs, each of the structurally different RNP complexes comprises a Cas9 nickase, and the structurally different guide RNAs hybridize to opposite strands of the target region.

In some embodiments, at least two structurally different nucleic acids encoding a variable region of a heterologous TCR-β chain and a variable region of a heterologous TCR-α chain are introduced into exon 1 of the TRAC gene in a population of T cells. In this way, a plurality of nucleic acid sequences, wherein each nucleic acid sequence encodes a unique combination of a heterologous TCR-β chain and a heterologous TCR-α chain, can be introduced into a population of T cells. Each of the nucleic acid sequences can be introduced into the cell as part of an RNP-DNA template complex.

For example, a targeted nuclease can be complexed with a plurality (e.g., 2, 3, 4, 5, or more, e.g., 2-10, 5-100, 20-100) of unique DNA templates encoding a variable region of a heterologous TCR-β chain and a variable region of a heterologous TCR-α chain. The plurality of complexes can be simultaneously introduced into a population of T cells to insert a single DNA template encoding a unique combination of a variable region of a heterologous TCR-β chain and a variable region of a heterologous TCR-α chain into exon 1 of the TRAC gene in individual T cells. Although each T cell will only acquire a single DNA template, across the population of cells, many of the unique, structurally different DNA templates will be integrated into the T cells to create a library of heterologous TCR sequences.

In some embodiments where separate constructs are used to insert a heterologous TCR-α chain into exon 1 of the TRAC gene and a heterologous TCR-β chain into exon 1 of the TRBC gene, a first targeted nuclease can be complexed with a plurality of unique DNA templates encoding a variable region of a heterologous TCR-β chain to form a plurality of first RNP-DNA template complexes, and a second targeted nuclease can be complexed with a plurality of unique DNA templates encoding a variable region of a heterologous TCR-α chain to form a plurality of second RNP-DNA template complexes. The first and second plurality of complexes can be simultaneously introduced into a population of T cells to create a library of heterologous TCR sequences.

The heterologous T cell repertoire can be designed and generated from previously known TCR sequences as well as from natural repertoires found in endogenous T cell populations of interest. For example, the TCR sequences can be TCR sequences obtained from tumor infiltrating lymphocytes, from autoreactive T cells at sites of autoimmune disease or from pathogen responsive T cells.

In some embodiments, the nucleic acid sequence or RNP-DNA template complex are introduced into about $1\times10^5$ to about $2\times10^6$ cells T cells. For example, the nucleic acid sequence or RNP-DNA template complex can be introduced into about $1\times10^5$ cells to about $5\times10^5$ cells, about $1\times10^5$ cells to about $1\times10^6$ cells, $1\times10^5$ cells to about $1.5\times10^6$ cells, $1\times10^5$ cells to about $2\times10^6$ cells, about $1\times10^6$ cells to about $1.5\times10^6$ cells or about $1\times10^6$ cells to about $2\times10^6$ cells.

In the methods and compositions provided herein, the human T cells can be primary T cells. In some embodiments, the T cell is a regulatory T cell, an effector T cell, or a naïve T cell. In some embodiments, the effector T cell is a $CD8^+$ T cell. In some embodiments, the T cell is a $CD4^+CD8^+$ T cell. Populations of any of the cells modified by any of the methods described herein are also provided. The cell can be in vitro, ex vivo or in vivo. In some cases, T cells are removed from a subject, modified using any of the methods described herein and administered to the patient.

In some embodiments, the modified T cells are cultured under conditions that allow expression of the heterologous TCR-β chain and the heterologous TCR-α chain to form a heterologous antigen-specific T cell receptor. In other embodiments, the T cells are cultured under conditions effective for expanding the population of modified cells. In some embodiments, T cells that express the antigen-specific T cell receptor are purified.

Compositions

Also provided are human T cells produced by any of the methods provided herein. Populations of human T cells produced by any of the methods provided herein are also provided. Further provided is a plurality of human T cells, wherein the genome of at least 20%, 30%, 40%, 50%, 60%, 70%, 80%, 90%, 95%, 99% or greater of the cells comprises a targeted insertion of a heterologous nucleic acid, wherein the nucleic acid is inserted into exon 1 of the TRAC or exon 1 of the TRBC. In some embodiments, the T cells are regulatory T cells, effector T cells, or naïve T cells. In some embodiments, the effector T cells are $CD8^+$ T cells. In some embodiments, the effector T cells are $CD4^+CD8^+$ T cells.

Also provided is a T cell comprising a nucleic acid sequence encoding, from the N-terminus to the C-terminus, (i) a first self-cleaving peptide sequence; (ii) a first heterologous, TCR subunit chain, wherein the TCR subunit chain comprises the constant region and the variable region of the TCR subunit chain, (iii) a second self-cleaving peptide sequence; (iv) a variable region of a second, heterologous TCR subunit chain; and (v) a portion of the N-terminus of the endogenous TCR subunit, wherein, if the endogenous TCR subunit is a TCR-alpha (TCR-α) subunit, the first heterologous TCR subunit chain is a heterologous TCR-beta (TCR-β) subunit chain and the second heterologous TCR subunit chain is a heterologous TCR-α subunit chain, and wherein if the endogenous TCR subunit is a TCR-β subunit, the first heterologous TCR subunit chain is a heterologous TCR-α subunit chain and the second heterologous TCR subunit chain is a heterologous TCR-β subunit chain. In some embodiments, the nucleic acid sequence encodes, from the N-terminus to the C-terminus, (i) a first self-cleaving peptide sequence, (ii) a heterologous TCR-β subunit chain, (iii) a second self-cleaving peptide sequence; (iv) a variable region of a heterologous TCR-α subunit chain, and (v) a portion of the N-terminus of the endogenous TCR-α subunit chain. In some examples, the nucleic acid encodes, from the N-terminus to the C-terminus, (i) a first self-cleaving peptide sequence, (ii) a heterologous TCR-α subunit chain, (iii) a second self-cleaving peptide sequence, (iv) a variable region of a heterologous TCR-β subunit chain, and (v) a portion of the N-terminus of the endogenous TCR-β subunit.

Also provided is a modified T cell comprising a nucleic acid sequence encoding, from the N-terminus to the C-terminus, (i) a first self-cleaving peptide sequence; (ii) a variable region of a heterologous TCR-β chain; (iii) a second self-cleaving peptide sequence; (iv) a variable region of a heterologous TCR-α chain; and (v) a portion of the N-terminus of the endogenous TCR-α subunit, wherein the nucleic acid sequence is integrated into exon 1 of the TRAC gene. In some examples, the nucleic acid encodes, from the N-terminus to the C-terminus, a first-self-cleaving peptide sequence, a heterologous (e.g., full-length) TCR-β subunit chain, a second self-cleaving peptide sequence and a variable region of a heterologous TCR-α subunit chain.

Also provided is a modified T cell comprising a nucleic acid sequence encoding, from the N-terminus to the C-terminus, (i) a first self-cleaving peptide sequence; (ii) a variable region of a heterologous TCR-α chain; (iii) a second self-cleaving peptide sequence; (iv) a variable region of a heterologous TCR-β chain; and (v) a portion of the N-terminus of the endogenous TCR-β subunit, wherein the nucleic acid sequence is integrated into exon 1 of the TRBC gene. In other examples, the nucleic acid encodes, from the N-terminus to the C-terminus, a first self-cleaving peptide sequence, a heterologous (e.g., full-length) TCR-α subunit chain, a second self-cleaving peptide sequence and a variable region of a heterologous TCR-β subunit chain.

Also provided is a modified T cell comprising a nucleic acid sequence encoding, from the N-terminus to the C-terminus, (i) a first self-cleaving peptide sequence; (ii) a variable region of a heterologous TCR-β chain; (iii) a second self-cleaving peptide sequence; (iv) a variable region of a heterologous TCR-α chain; and (v) a portion of the N-terminus of the endogenous TCR-γ subunit, wherein the nucleic acid sequence is integrated into exon 1 of exon 1 of the TRGC gene.

Further provided is a modified T cell comprising: a) a first nucleic acid sequence encoding, from N-terminus to C-terminus, (i) a first self-cleaving sequence, (ii) a variable region of a heterologous TCR-α chain, and (iii) a portion of the N-terminus of the endogenous TCR-α chain; and b) a second nucleic acid sequence encoding, from N-terminus to C-terminus, (i) a first self-cleaving sequence, (ii) a variable region of a heterologous TCR-chain, and (iii) a portion of the N-terminus of the endogenous TCR-β chain, wherein the first nucleic acid sequence is integrated into exon 1 of the TRAC gene and the second nucleic sequence is integrated into exon 1 of the TRBC gene.

Methods of Treatment

Any of the methods and compositions described herein can be used to treat or prevent a disease (e.g., cancer, an infectious disease, an autoimmune disease, transplantation rejection, graft vs. host disease or other inflammatory disorder in a subject). In the methods of treatment provided herein, a nucleic acid sequence comprising the TCR-α or the TCR-β chain of a TCR in a subject having, for example, cancer, an infectious disease, an autoimmune disease, the potential for transplantation rejection, graft vs. host disease or other inflammatory disorder, can be obtained from T cells in the subject. For example, tumor infiltrating lymphocytes, T cells at autoimmune sites or from pathogen responsive lymphocytes can be isolated from the subject to obtain a nucleic acid sequence comprising the TCR-α or the TCR-β chain of a TCR. In some embodiments, monoclonal or polyclonal TCR sequences identified from patient samples can be used. For example, TCR repertoires from tumor or inflamed sites can be obtained and cells with these antigen specificities can be made by synthesizing the TCR sequences and using them as DNA templates. Alternatively, the sequences can be amplified, for example, PCR-amplified, from clones/single cells from the subject and the amplified sequences can be used as DNA templates. Once the sequences of the TCR-α and TCR-β chain of TCRs are obtained, these sequences can be inserted into a population of T cells in or from the subject to replace the endogenous TCR of T cells in the subject with a heterologous TCR of desired antigen specificity. In some embodiments, a population of modified T cells can be administered to the subject to treat the disease. See, for example, FIG. 3B.

Provided herein is a method of treating cancer in a human subject comprising: modifying the T cells of the subject using any of the methods described herein to express an antigen-specific T cell receptor, wherein the T cell receptor recognizes a tumor-specific antigen in the subject.

In some embodiments, the cancer to be treated is selected from a cancer of B-cell origin, breast cancer, gastric cancer, neuroblastoma, osteosarcoma, lung cancer, colon cancer, chronic myeloid cancer, leukemia (e.g., acute myeloid leukemia, chronic lymphocytic leukemia (CLL) or acute lymphocytic leukemia (ALL)), prostate cancer, colon cancer, renal cell carcinoma, liver cancer, kidney cancer, ovarian cancer, stomach cancer, testicular cancer, rhabdomyosarcoma, and Hodgkin's lymphoma. In some embodiments, the cancer of B-cell origin is selected from the group consisting of B-lineage acute lymphoblastic leukemia, B-cell chronic lymphocytic leukemia, and B-cell non-Hodgkin's lymphoma.

In some embodiments of the methods of treatment described herein, for example, treatment of cancer, infectious disease or an autoimmune disorder, the T cells are modified in vivo. Any of the constructs described herein is delivered to the patient in vivo. See, for example, U.S. Pat. No. 9,737,604 and Zhang et al. "Lipid nanoparticle-mediated efficient delivery of CRISPR/Cas9 for tumor therapy," NPG Asia Materials Volume 9, page e441 (2017).

In some embodiments, the method of treating cancer in a human subject comprises: a) obtaining T cells from the subject; b) modifying the T cells using any of the methods provided herein to express a heterologous antigen-specific T cell receptor, wherein the T cell receptor recognizes a tumor-specific antigen in the subject; and c) administering the modified T cells to the subject. As used throughout, the phrase "tumor-specific antigen" means an antigen that is unique to cancer cells or is expressed more abundantly in cancer cells than in in non-cancerous cells.

Further provided herein is a method of treating an autoimmune disease in a human subject comprising: modifying the T cells of the subject using any of the methods described herein to express a heterologous antigen-specific T cell receptor, wherein the T cell receptor recognizes an antigen associated with the autoimmune disorder.

In some embodiments, the method of treating an autoimmune disease in a human subject comprises: a) obtaining T cells from the subject; b) modifying the T cells using any of the methods provided herein to express a heterologous antigen-specific T cell receptor, wherein the T cell receptor recognizes an antigen associated with the autoimmune disorder in the subject; and c) administering the modified T cells to the subject. In some embodiments, the T cells are regulatory T cells.

Further provided herein is a method of treating an infection in a human subject comprising: modifying the T cells of the subject using any of the methods described herein to express a heterologous antigen-specific T cell receptor, wherein the T cell receptor recognizes an antigen associated with the infection in the subject.

In some embodiments, the method of treating an infection in a human subject comprises: a) obtaining T cells from the subject; b) modifying the T cells using any of the methods provided herein to express a heterologous antigen-specific T cell receptor, wherein the T cell receptor recognizes an antigen associated with the infection in the subject; and c) administering the modified T cells to the subject.

Any of the methods of treatment provided herein can further comprise expanding the population of T cells before the endogenous TCR is replaced with a heterologous TCR. Any of the methods of treatment provided herein can further comprise expanding the population of T cells after the endogenous TCR is replaced with a heterologous TCR and prior to administration to the subject.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to one or more molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

The following examples are provided by way of illustration only and not by way of limitation. Those of skill in the art will readily recognize a variety of non-critical parameters that could be changed or modified to yield essentially the same or similar results.

Isolation of Human Primary T Cells for Gene Targeting

Primary human T cells were isolated from healthy human donors either from fresh whole blood samples, residuals from leukoreduction chambers after Trima Apheresis (Blood Centers of the Pacific), or leukapheresis products (StemCell). Peripheral blood mononuclear cells (PBMCs) were isolated from whole blood samples by Ficoll centrifugation using SepMate tubes (STEMCELL, per manufacturer's instructions). T cells were isolated from PBMCs from all cell sources by magnetic negative selection using an EasySep Human T Cell Isolation Kit (STEMCELL, per manufacturer's instructions). Unless otherwise noted, isolated T cells were stimulated and used directly (fresh). When frozen cells were used, previously isolated T cells that had been frozen in Bambanker freezing medium (Bulldog Bio) per manufacturer's instructions were thawed, cultured in media without stimulation for 1 day, and then stimulated and handled as described for freshly isolated samples. Fresh healthy human blood donors were consented under protocol approved by the UCSF Committee on Human Research (CHR). Patient samples for gene editing were obtained under a protocol approved by the Yale Internal Review Board (IRB).

Primary T Cell Culture

Unless otherwise noted, bulk T cells were cultured in XVivo™ 15 medium (STEMCELL) with 5% Fetal Bovine Serum, 50 mM 2-mercaptoethanol, and 10 mM N-Acetyl L-Cystine. Serum free media (ImmunoCult XF T cell expansion media, STEMCELL) without additives, as well as RPMI+10% FBS were used in indicated experiments (FIG. 15). Immediately following isolation, T cells were stimulated for 2 days with anti-human CD3/CD28 magnetic dynabeads (ThermoFisher) at a beads to cells concentration of 1:1, along with a cytokine cocktail of IL-2 at 200 U/mL (UCSF Pharmacy), IL-7 at 5 ng/mL (ThermoFisher), and IL-15 at 5 ng/mL (Life Tech). Following electroporation, T cells were cultured in media with IL-2 at 500 U/mL. Throughout culture T cells were maintained at an approximate density of 1 million cells per mL of media. Every 2-3 days post-electroporation additional media was added, along with additional fresh IL-2 to bring the final concentration to 500 U/mL, and cells were transferred to larger culture vessels as necessary to maintain a density of 1 million cells/mL.

RNP Production

RNPs were produced by annealing of a two-component gRNA to Cas9, as previously described (Schumann et al. PNAS 112: 10437-10442 (2015); and Hultquist et al. *Cell Rep.* 17: 1438-1452 (2016))). Briefly, crRNAs and tracrRNAs were chemically synthesized (Dharmacon, IDT), and recombinant Cas9-NLS, D10A-NLS, or dCas9-NLS were recombinantly produced and purified (QB3 Macrolab). Lyophilized RNA was resuspended in Tris-HCL (7.4 pH) with 150 mM KCl at a concentration of 160 uM, and stored in aliquots at −80 C. crRNA and tracrRNA aliquots were thawed, mixed 1:1 by volume, and incubated at 37 C for 30 min to form an 80 uM gRNA solution. Recombinant Cas9 and variants, stored at 40 uM in 20 mM HEPES-KOH pH 7.5, 150 mM KCl, 10% glycerol, 1 mM DTT, were then mixed 1:1 by volume with the 80 uM gRNA (2:1 gRNA to Cas9 molar ratio) at 37° C. for 15 min to form an RNP at 20 uM. RNPs were generally electroporated immediately after complexing.

dsDNA HDRT Production

Double stranded DNA HDRT sequences were generated from PCR products. Novel HDR sequences were constructed using Gibson Assemblies to place the HDR template sequence, consisting of the homology arms (commonly synthesized as gBlocks from IDT) and the desired insert (such as GFP) into a cloning vector for sequence confirmation and future propagation. These plasmids were used as templates for high-output PCR amplification (Kapa Hotstart polymerase). PCR amplicons (the dsDNA HDRT) were SPRI purified (1.0×) and eluted into a final volume of 3 μL H2O per 100 μL of PCR reaction input. Concentrations of HDRTs were analyzed by nanodrop with a 1:20 dilution. The size of the amplified HDRT was confirmed by gel electrophoresis in a 1.0% agarose gel.

ssDNA HDRT Production by Exonuclease Digestion

To produce long ssDNA as HDR donors, the DNA of interest was amplified via PCR using one regular, non-modified PCR primer and a second phosphorylated PCR primer. The DNA strand that will be amplified using the phosphorylated primer, will be the strand that will be degraded using this method. This allows to either prepare a single stranded sense or single stranded antisense DNA using the respective phosphorylated PCR primer. To produce the ssDNA strand of interest, the phosphorylated strand of the PCR product was degraded via subsequent treatment with two enzymes, Strandase Mix A and Strandase Mix B, for 5 minutes (per 1 kb) at 37° C., respectively. Enzymes were deactivated by a 5 minute incubation at 80 C. Resulting ssDNA HDR templates were SPRI purified (1.0×) and eluted in H2O. A more detailed protocol for the Guide-it™ Long ssDNA Production System (Takara Bio USA, Inc. #632644) can be found at the manufacturer's website.

ssDNA HDRT Production by Reverse Synthesis ssDNA donors were synthesized by reverse transcription of an RNA intermediate followed by hydrolysis of the RNA strand in the resulting RNA:DNA hybrid product, as described in Leonetti et al. http://www.biorxiv.org/content/early/2017/08/21/178905). Briefly, the desired HDR donor was first cloned downstream of a T7 promoter and the T7-HDR donor sequence amplified by PCR. RNA was synthesized by in vitro transcription using HiScribe T7 RNA polymerase (New England Biolabs) and reverse-transcribed using TGIRT-III (InGex). Following reverse transcription, NaOH and EDTA were added to 0.2 M and 0.1 M respectively and RNA hydrolysis carried out at 95° C. for 10 min. The reaction was quenched with HCl, the final ssDNA product purified using Ampure XP magnetic beads (Beckman Coulter) and eluted in sterile RNAse-free H2O. ssDNA quality was analyzed by capillary electrophoresis (Bioanalyzer, Agilent).

Primary T Cell Electroporations

RNPs and HDR templates were electroporated 2 days following initial T cell stimulation. T cells were harvested from their culture vessels and magnetic CD3/CD28 dynabeads were removed by placing cells on a magnet for 2 minutes. Immediately prior to electroporation, de-beaded cells were centrifuged for 10 minutes at 90×g, aspirated, and resuspended in the Lonza electroporation buffer P3 at 20 μL buffer per one million cells. For optimal editing, one million T cells were electroporated per well using a Lonza 4D 96-well electroporation system with pulse code EH115. Alternate cell concentrations from 200,000 up to 2 million cells per well showed lower efficiencies. Alternate electroporation buffers were used as indicated, but had different optimal pulse settings (E0155 for OMEM buffer). Unless otherwise indicated, 2.5 μLs of RNPs (50 pmols total) were electroporated, along with 2 μLs of HDR Template at 2 μgs/μL (4 μgs HDR Template total).

For 96-well experiments, HDRTs were first aliquoted into wells of a 96-well polypropylene V-bottom plate. RNPs were then added to the HDRTs and allowed to incubate together at RT for at least 30 seconds. Finally, cells resuspended in electroporation buffer were added, briefly mixed by pipetting with the HDRT and RNP, and 24 μLs of total volume (cells+RNP+HDRT) was transferred into a 96 well electroporation cuvette plate. Immediately following electroporation, 80 μLs of pre-warmed media (without cytokines) was added to each well, and cells were allowed to rest for 15 minutes at 37° C. in a cell culture incubator while remaining in the electroporation cuvettes. After 15 minutes, cells were moved to final culture vessels.

Non-Viral Replacement of Endogenous T Cell Receptor with Single HDR Template

Figure 1B:
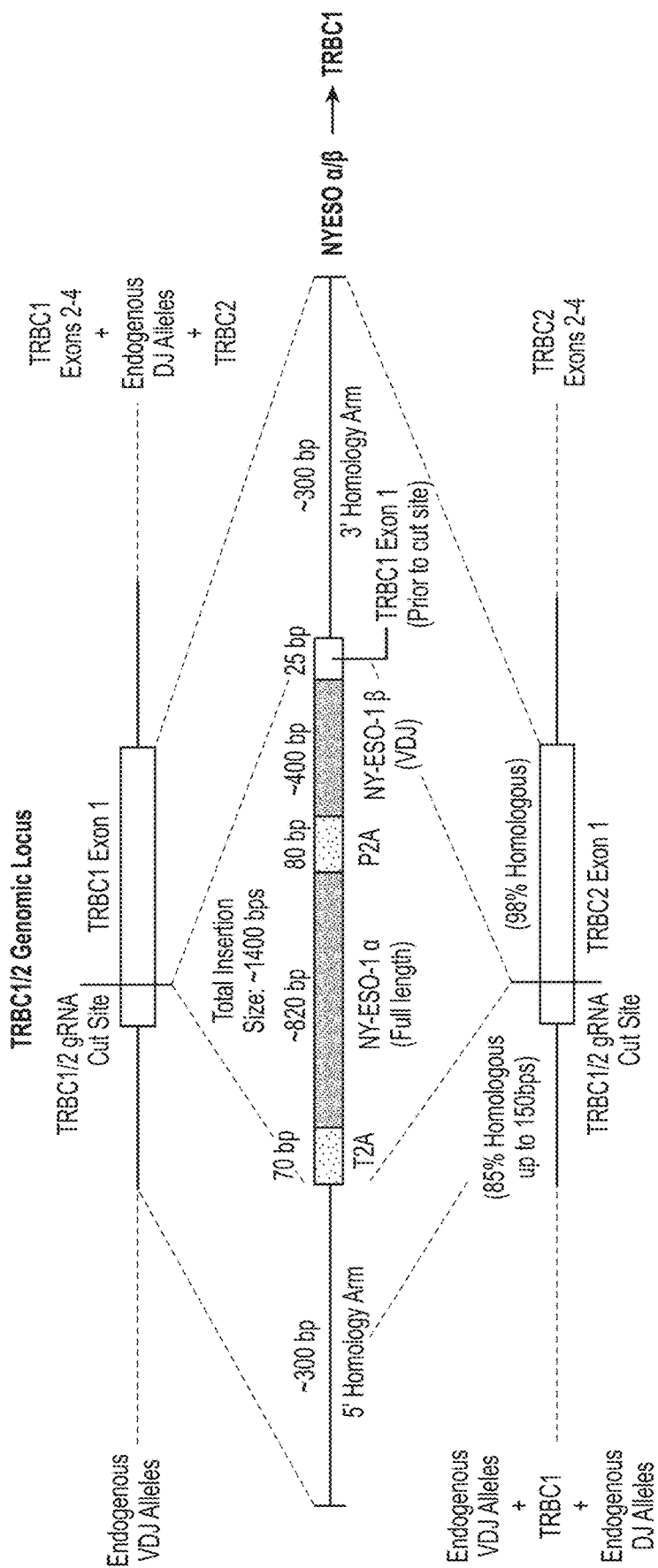
FIG. 1B is a schematic depicting insertion of a single non-viral DNA template at the TCR-β locus (TRBC1 or TRBC2). The template comprises a nucleic acid sequence encoding, from the N-terminus to the C-terminus, (i) a T2A self-cleaving peptide sequence; (ii) a full-length (i.e, variable region and constant region) heterologous TCR-α chain (NYESO-α); (iii) a P2A self-cleaving peptide sequence; (iv) a variable region of a heterologous TCR-β chain (NYESO-β); and (v) a portion of the N-terminus of the endogenous TCR beta subunit into a T cell via homology directed repair.
Figure 2:
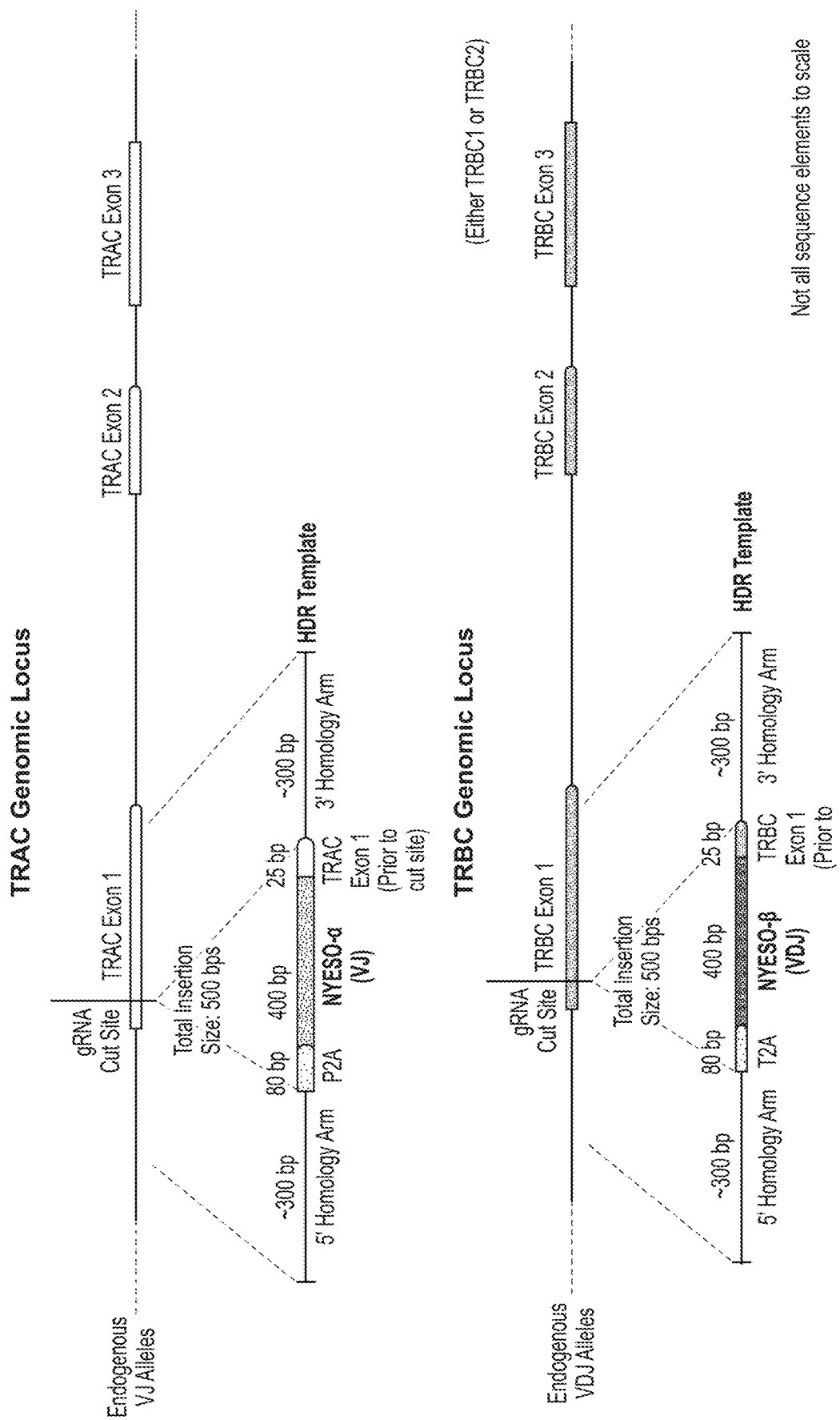
FIG. 2 is a schematic depicting simultaneous replacement of both the endogenous T cell a and T cell receptor chains by inserting (a) a non-viral DNA template comprising a nucleic acid sequence encoding, from the N-terminus to the C-terminus, (i) a P2A self-cleaving peptide sequence, (ii) a variable region of a TCR-α chain of an antigen specific T cell receptor (NYESO-α); and (iii) a portion of the N-terminus of exon 1 of the endogenous TCR-α subunit; and (b) a DNA template comprising a nucleic acid sequence encoding, from the N-terminus to the C-terminus, (i) a T2A self-cleaving peptide sequence, (ii) a variable region of a TCR-β chain of an antigen specific T cell receptor; and (iii) a portion of the N-terminus of exon 1 of the endogenous TCR-β subunit.

Both the TCR-α and TCR-β chains can be knocked in simultaneously in a single multiplexed round of editing (FIG. 2). This is similar to the targeting strategy in FIG. 1A and FIG. 1B, except that at both the TCR-α and TCR-β constant loci, only the variable regions of the desired antigen specific TCR are inserted. This has the benefit of both reducing the total size of the insertions (from one 1.5 kbp insertion to two 500 bp insertions), but also means that any T cell expressing both chains of the desired antigen specific TCR will have both its previously recombined endogenous TCR-α and TCR-β chains knocked out, preventing the potentially undesirable pairing of an inserted antigen specific TCR-α chain with an endogenous TCR-β chain for example.

Endogenous TCR Replacement with a Polyclonal Library of T Cell Receptors

Figure 3A:
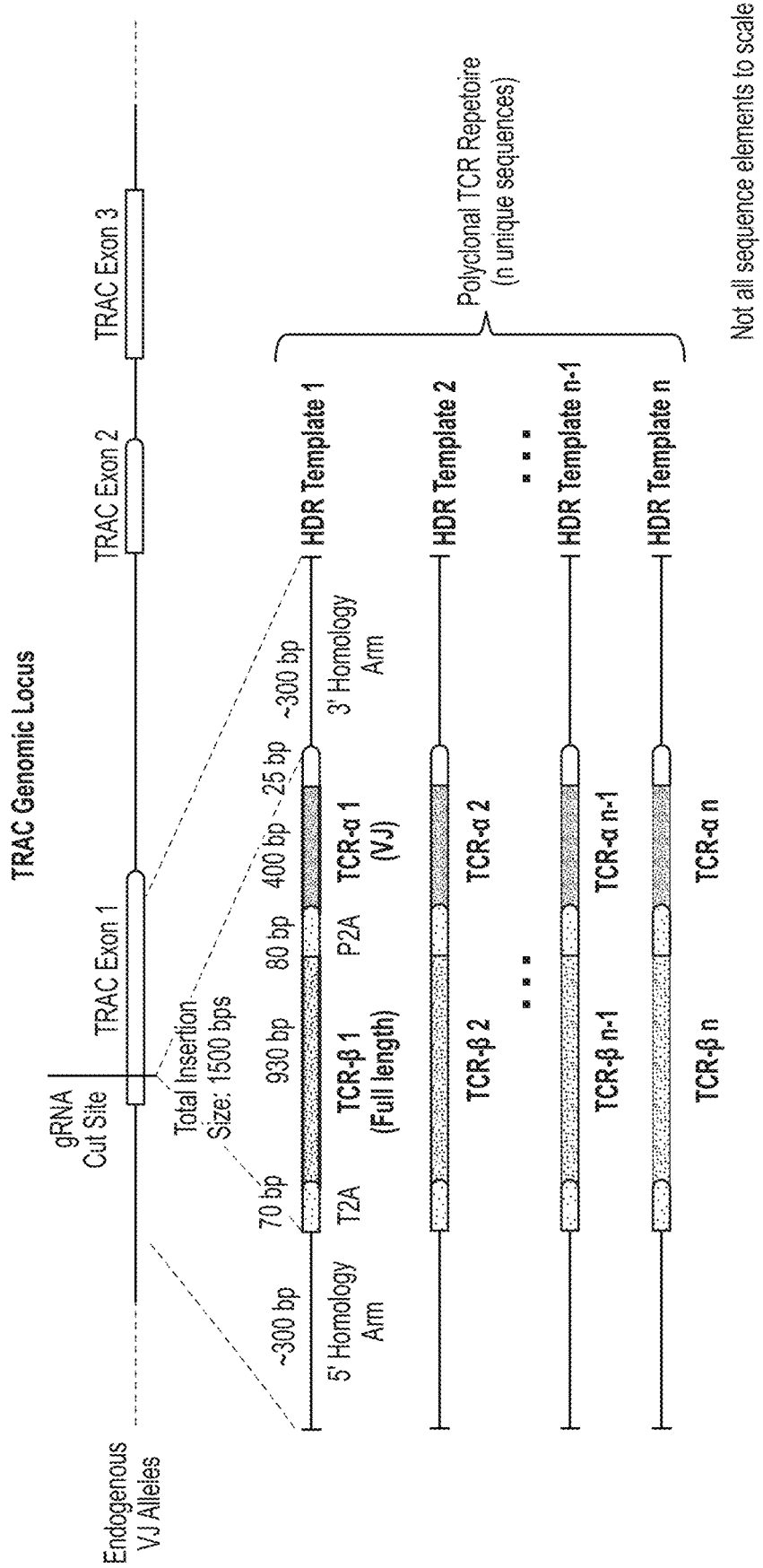
FIG. 3A is a schematic depicting insertion of a heterologous (TCR)-β chains and TCR-α chain in T cells to form a polyclonal library of T cell receptors. Multiple, different DNA templates, for example, non-viral DNA templates, containing a nucleic acid sequence encoding, from the N-terminus to the C-terminus, (i) a first self-cleaving peptide sequence; (ii) a full-length (e.g. variable region and constant region) heterologous T cell receptor (TCR)-β chain; (iii) a second self-cleaving peptide sequence; (iv) a variable region of a heterologous TCR-α chain; and (v) a portion of the N-terminus of the endogenous TCR alpha subunit were simultaneously electroporated to produce a population of T cells with a synthetic T cell repertoire of desired TCR sequences.

Since the gRNA and homology arms are the same for replacement of the endogenous TCR with any desired new, heterologous TCR sequence, multiple different DNA templates containing a variety of desired TCRs can be electroporated simultaneously. While any specific T cell will only acquire a single TCR from the variety of desired TCRs, many of the TCR DNA templates will be integrated across the population of electroporated cells, thus creating a synthetic T cell repertoire of desired sequences (FIG. 3A).

Figure 3B:
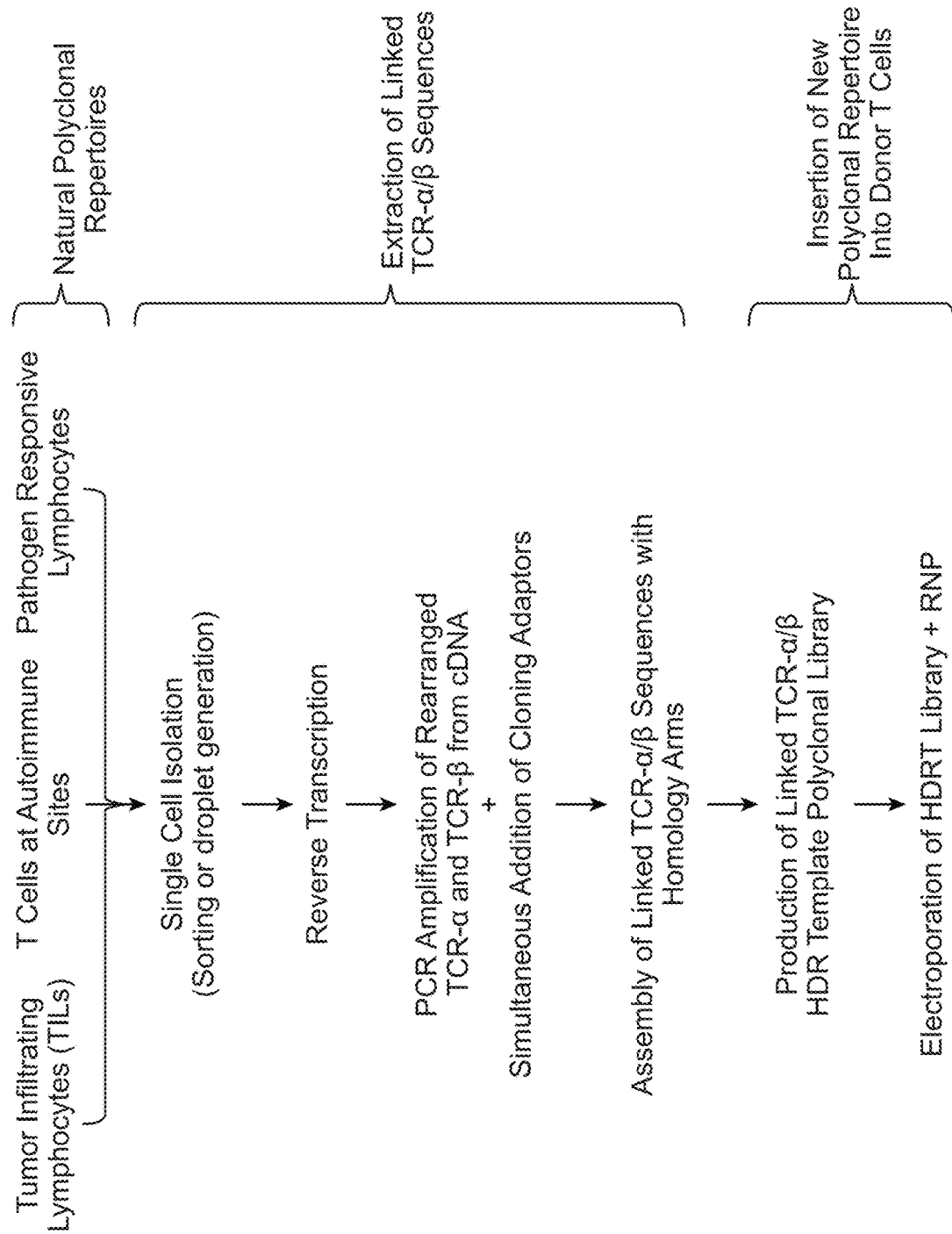
FIG. 3B is a schematic showing the design of a T cell repertoire from previously known TCR sequences, or from natural repertoires in endogenous T cell populations of interest, for example, from a subject. For example, the TCRs can be, but are not limited to, TCRs expressed by tumor infiltrating lymphocytes, TCRs expressed by autoreactive T cells at sites of autoimmune disease or TCRs from pathogen responsive T cells.

A synthetic T cell repertoire can be designed and generated from previously known TCR sequences or from natural repertoires found in endogenous T cell populations of interest (FIG. 3B). Some examples include the TCRs expressed by tumor infiltrating lymphocytes (to be inserted into a new population of CD8+ or CD4+ T cell effectors), the TCRs expressed by autoreactive T cells at sites of autoimmune disease (to be inserted into a population of regulatory T cells), or TCRs from pathogen responsive T cells (inserted into CD8+ or CD4+ T cell effectors).

Non-Viral Replacement of Endogenous T Cell Receptor with Single HDR Template

The genomic locus of the T cell receptor is extremely complicated, with a large variety of variable alleles (termed V and J alleles for the TCR-α chain and V, D and J alleles for the TCR-β chain) that undergo somatic gene rearrangement during T cell development in order to produce a functional T cell receptor. Important for the diversity of the TCR repertoire, but challenging for targeted genomic editing at the TCR locus (whether knock-outs or knock-ins), these recombined sequences are different across the polyclonal population of T cells. For targeting applications, for both the TCR-α and TCR-β chains there is a constant domain at the C-terminus of the protein that is shared by all T cells, no matter what V-J or V-D-J segments have been rearranged. The TCR-β locus has two constant regions (TRBC1 and TRBC2) that can be targeted as shown in FIG. 1B. This constant sequence (constant exons, labeled TRAC or TRBC Exon 1, Exon 2, etc.) allows for a single set of genomic targeting reagents (CRISPR/Cas9 system in this application, i.e., a single gRNA sequence) to be used to modify every T cell no matter what rearranged TCR they express.

Using the methods set forth above, a DNA template encoding a heterologous TCR that specifically binds to a tumor antigen was made and used to replace an endogenous TCR in a human T cell. The homology directed repair template (either dsDNA produced by PCR or ssDNA produced by a variety of methods described herein) used to replace the endogenous TCR is ~2.1 kb long, including 5' and 3' homology arms (~300 bp) that are homologous to the genomic sequences flanking the gRNA cut site (FIG. 1A). Between these homology arms is a ~1.5 kb sequence that was inserted at the gRNA cut site by homology directed repair. This inserted sequence starts with a multicistronic element (a T2A self-excision peptide), followed by the full length sequence of the TCR-0 chain of the desired antigen specific T cell receptor (in this example, a TCR specific to the NY-ESO-1 melanoma neoantigen). A second multicistronic element (a P2A self excision peptide) follows the TCR-β chain, and separates it from the variable (recombined V and J alleles) sequence of the desired antigen specific TCR-α chain. Only the variable region from the TCR-α chain and the sequence of the TRAC exon 1 to the prior to (the 5' end of) the gRNA cut site were inserted, as the remaining TRAC exons were spliced together into the final mRNA sequence. The DNA template was introduced into the T cells as part of an RNP:DNA template complex as described above.

Transcription in cells with successful HDR yielded a polycistronic mRNA encoding both TCR-β and TCR-α. This targeting strategy yielded three peptide chains– (1) a remnant endogenous variable region peptide that does not possess a transmembrane pass (and thus should not be expressed on the cell surface) and was degraded in the endoplasmic reticulum or secreted following transcription; (2) the full length desired antigen-specific TCR-β chain; and (3) the full length desired antigen-specific TCR-α chain. The result was a T cell that expressed both chains of a desired antigen specific TCR under the control of the endogenous TCR promoter. Both chains were expressed by the T cell to form a heterologous TCR that specifically recognized the NY-ESO-1 melanoma neoantigen.

Figure 4A:
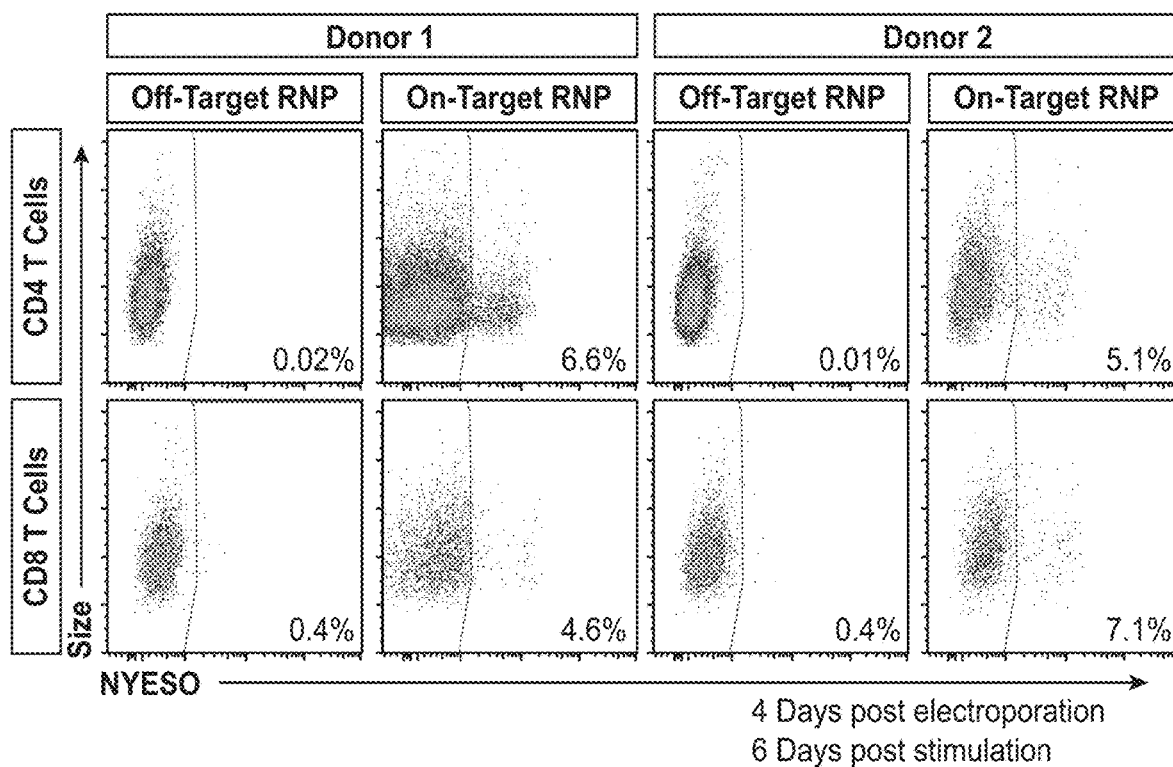
FIG. 4A shows FACS analysis of $CD4^+$ and $CD8^+$ T cells electroporated with a heterologous NYESO TCR. $CD4^+$ and $CD8^+$ T cells from two healthy human blood donors were electroporated with a non-viral construct comprising a heterologous NYESO- a and a heterologous NYESO-β, as described herein. Four days after electroporation, the cells were stained with a fluorescently labelled MHC-dextramer containing the peptide recognized by the integrated NYESO-specific TCR.
Figure 4B:
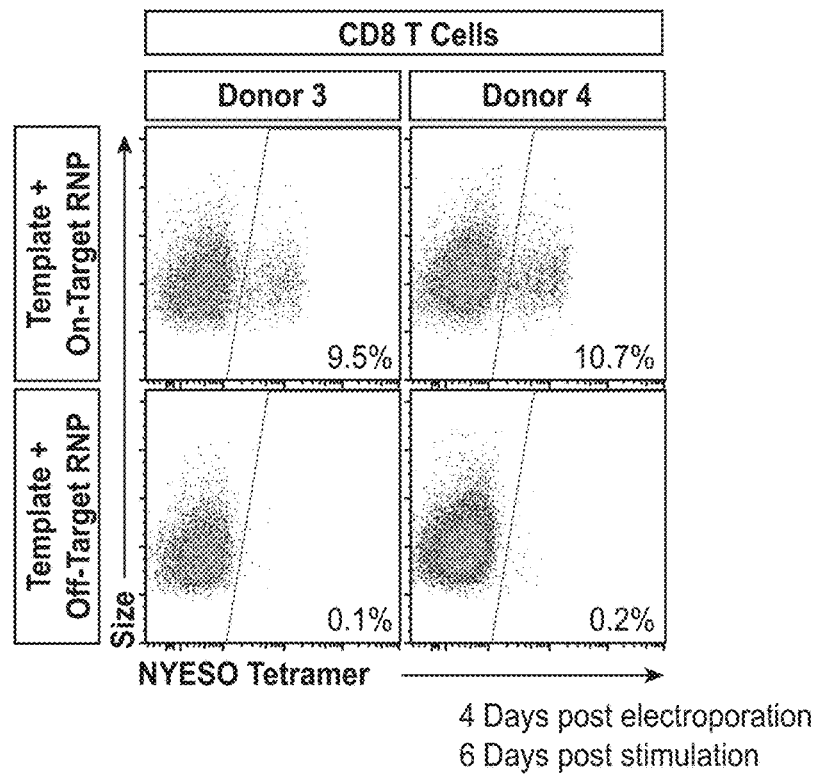
FIG. 4B shows FACS analysis of CD8+ T cells electroporated with a heterologous NYESO TCR. $CD8^+$ T cells from healthy human blood donors were electroporated with a non-viral DNA construct comprising a heterologous NYESO- a and a heterologous NYESO-β, as described herein. Four days after electroporation, the cells were stained with a fluorescently labelled MHC-dextramer containing the peptide recognized by the integrated NYESO-specific TCR.

As shown in FIG. 4A, four days after electroporation of the construct described above, CD4+ and CD8+ T cells from two healthy human blood donors were stained with a fluorescently labelled MHC-dextramer containing the peptide recognized by the integrated NY-ESO-1 specific TCR (NYESO). FIG. 4B is a second experiment showing similar results in other healthy human donors, thus demonstrating the robustness and reproducibility of non-viral endogenous TCR replacement.

TCR replacement was also accomplished at the TCR-β locus with a similar strategy to targeting TCR-α, although the β locus is more complex as there are two constant regions (TRBC1 and TRBC2) that are highly homologous to each another. An HDR template inserted a new full length TCR-α and the VDJ regions of a new TCR-β at the 5' end of the first TRBC1 exon using a gRNA targeting a sequence found in both TRBC1 and TRBC2. Due to the sequence similarity between the TRBC1 and TRBC2 genomic regions, the 3' homology arm of this construct was almost perfectly homologous as well to the equivalent region in TRBC2, while the 5' homology arm had ~85% homology to the TRBC2 genomic region in the 150 bps closest to the insertion site. Insertion thus likely predominates at TRBC1, but is could also be possible at TRBC2 or with an intervening deletion between TRBC1 and TRBC2. gRNAs that cut specifically at TRBC1 or TRBC2 can also be used instead of the gRNA that targets both.

Figure 9A:
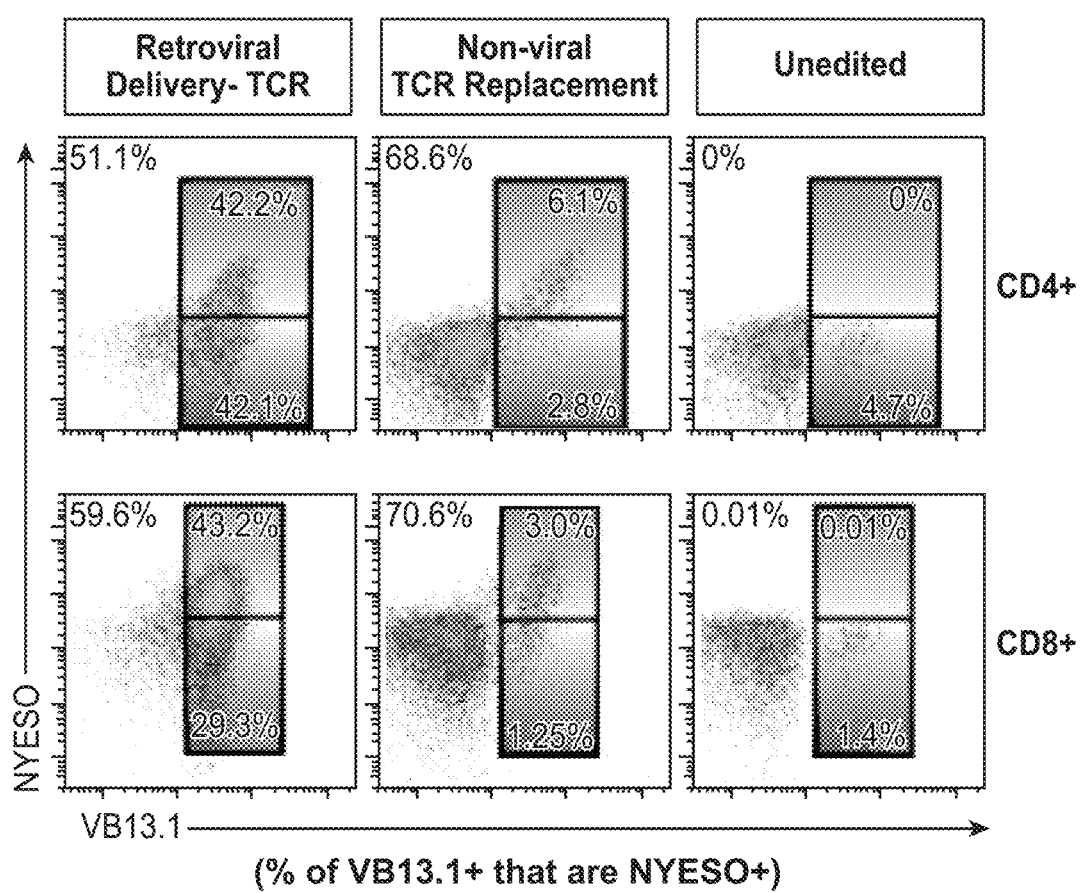
FIG. 9A shows TCR mispair analysis after retroviral delivery or non-viral TCR replacement of an NY-ESO-1 specific TCR in gated CD4+ or CD8+ T cells. Non-viral TCR replacement results in less TCR mispairing as compared to retroviral delivery of a TCR. With viral introduction of the new TCR, an infected cell will potentially express at least four different TCRs (new TCR-α+new TCR-β; new TCR-α+endogenous TCR-β; endogenous TCR-α and new TCR-β; endogenous TCR-α+endogenous TCR-β). Staining for the specific beta chain in the new introduced TCR (VB13.1) along with MHC-peptide multimer (NYESO) can provide a rough estimate of TCR mispairing by distinguishing between cells that predominantly expressed the introduced TCR (VB13.1+NYESO+; new TCR-α+new TCR-β) vs those that expressed predominantly one of the potential mispaired TCRs (VB13.1+NYESO−; endogenous TCR-α+ new TCR-β).

FIG. 9A shows TCR mispair analysis after retroviral delivery or non-viral TCR replacement of an NY-ESO-1 specific TCR in gated CD4+ or CD8+ T cells. Non-viral TCR replacement results in less TCR mispairing as compared to retroviral delivery of a TCR. Multiplexed replacement of the TCR, with a new TCR-α VJ domain targeted to TRAC and a new TRB-β VDJ domain targeted to TRBC1 was also possible and could present a strategy to further reduce TCR mispairing (FIGS. 9B-9C).

TCR Replacement with Dextramer and TCR Staining

Figure 5:
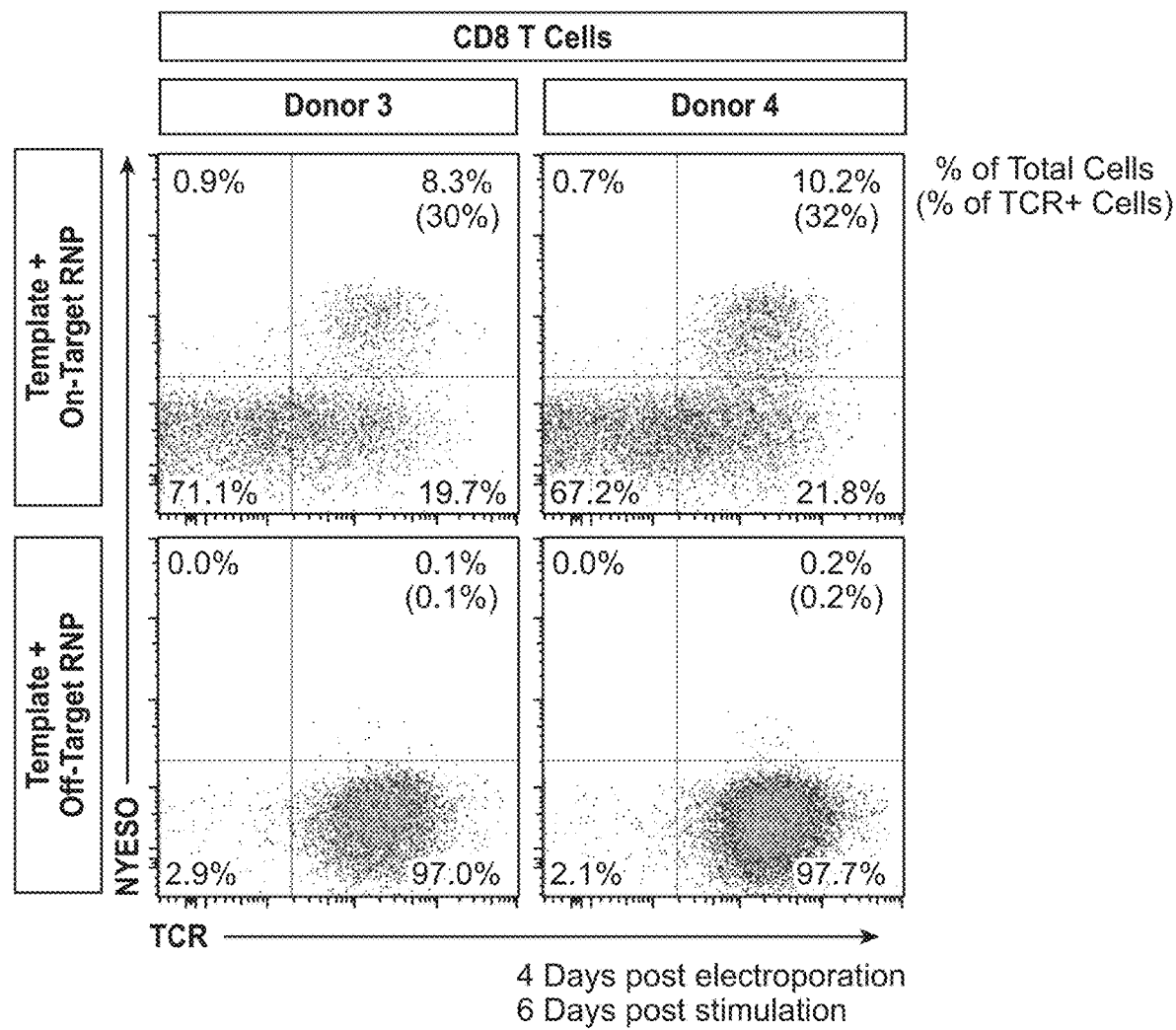
FIG. 5 is a FACS analysis of $CD8^+$ cells electroporated with a heterologous NYESO TCR. The cells were treated as in FIGS. 3 and 4, with the addition of staining for TCR expression (with an antibody that binds all potential human TCRs) against antigen specific staining with the NYESO MHC-dextramer. In the majority of T cells where there was not homology-directed replacement of the endogenous TCR, the endogenous TCR was knocked out due to cutting by the TRAC exon 1 gRNA and introduction of small insertion deletion mutations (indels) by non-homologous end joining. As expected, almost all of the NYESO positive cells were also positive for TCR expression.

CD4+ and CD8+ T cells from two healthy human blood donors were electroporated with a single construct as described above. Four days after electroporation, staining for TCR expression (with an antibody that binds all potential human TCRs) against antigen specific staining with the NYESO MHC-dextramer was performed. In the majority of T cells where there is not homology directed replacement of the endogenous TCR (FIG. 5), the endogenous TCR is knocked out due to cutting by the TRAC exon 1 gRNA and introduction of small indels by non-homologous end joining. As expected almost all NYESO positive cells are also positive for TCR expression.

In Vitro Cancer Cell Killing by TCR Knock-in Primary Human T Cells

Figure 6A:
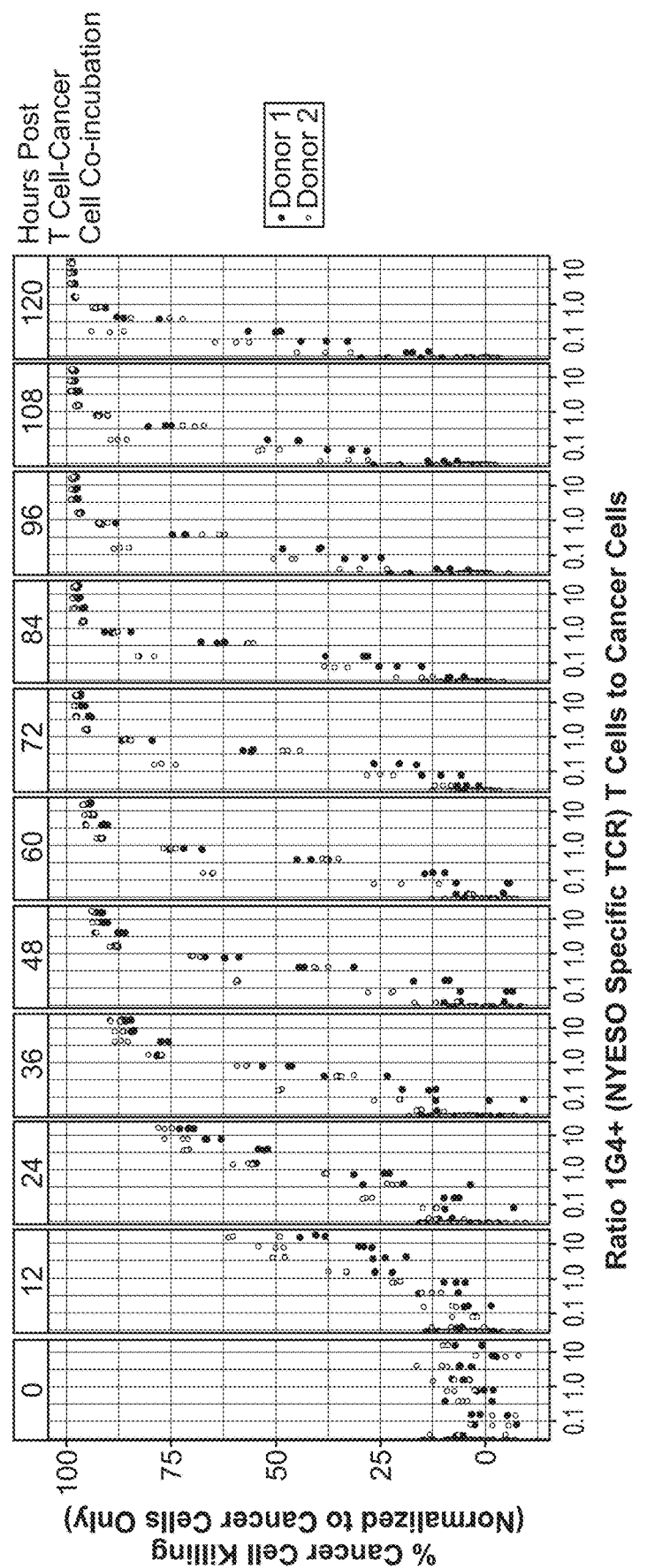
FIG. 6A shows that primary human T Cells containing a heterologous NYESO TCR kills cancer cells is an in vitro cell killing assay.

An in vitro cancer cell killing assay demonstrated the functional target cell killing capacity of TCR knock-in cells. As described above, the 1G4 (NYESO specific) TCR sequence was inserted into the endogenous TCR α locus in CD3+ primary T cells from healthy human donors. At 7 days post electroporation, cells were stained with a fluorescent NYESO peptide-MHC dextramer and NYESO+ cells were sorted by fluorescent activated cell sorting to achieve a pure population. This population was further cultured in standard T cell culture conditions (media and IL-2) for an additional five days. Twelve days post-electroporation, the sorted T cells with their endogenous TCR replaced by the 1G4 TCR were cocultured with a cancer cell line presenting the NYESO antigen on its MHC (A375 cells, derived from a melanoma, and endogenously expressing the NYESO antigen as well as MHC-A2, the MHC allele recognized by the 1G4 TCR). Every 12 hours, the number of cancer cells was counted by quantitative fluorescent imaging (the A375 cells express a Red Fluorescent Protein, allowing them to be specifically counted separately from the T cells). Fluorescent counts were automated using an Incucyte automated fluorescent microscope. The cultures were seeded with 3,000 cancer cells, and the indicated ratio of 1G4+ T cells (See FIG. 4A). In T cells edited from two healthy human donors, robust dose and time dependent killing of the target cancer cells was observed, indicating the functionality of the 1G4 TCR knock-in T cells. The percent killing of cancer cells was determined by dividing the number of live cancer cells in a given well by the number of live cancer cells in control wells that had no T cells present. High ratios (~10:1) of T cells to cancer cells showed rapid (<24 hours) killing of almost all cancer cells, but even very low ratios (~0.1:1) of T cells to cancer cells showed robust killing with additional time in culture (See FIG. 6A).

Figure 6B:
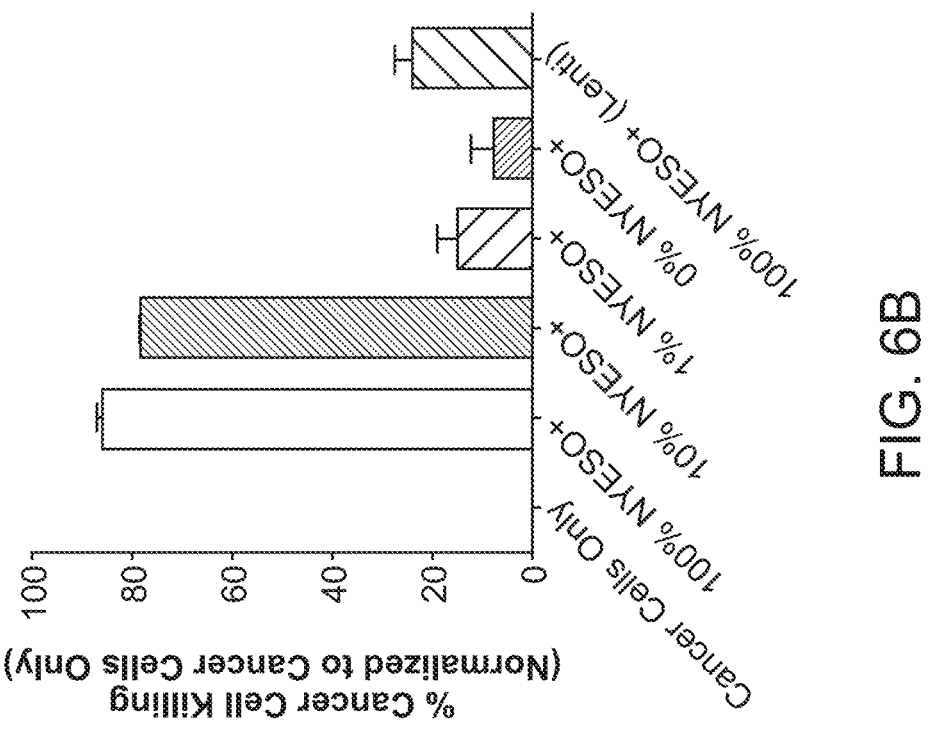
FIG. 6B shows the results from a single time point from an in vitro cell killing assay using human T Cells containing a heterologous NYESO TCR kills.

In vitro cancer killing by 1G4 TCR knock-in T cells at a single time point was demonstrated (See FIG. 6B). Summary data was taken from a single time point in the cell killing assays described above (36 hours post co-incubation). NYESO dextramer+(1G4+) T cells were sorted as described above, to generate a 100% 1G4 positive population, which was then diluted with NYESO dextramer− (1G4-) T cells from the same donor to yield the indicated percentages of NYESO+ staining T cells (10%, 1%, or 0%). Each of these populations was then co-cultured with cancer cells in an in vitro cancer killing assay, as described above, at a ratio of 8 T cells to 1 Cancer cell (yielding ratios of 8:1, 0.8:1, 0.08:1 and 0:1 1G4+ T cells: cancer cells for the 100%, 10%, 1%, and 0% NYESO+ T cell populations respectively). As a positive control for cancer cell killing, cells from an additional healthy donor were transduced with a lentivirus that randomly integrates a 1G4 TCR expression cassette into the genome of the T cells (it is noted that, in this case, the TCR is randomly integrated and expressed, as opposed to the 1G4 TCR knock-in T cells where the 1G4 TCR replaces the endogenous TCR locus, so that it is expressed off of the endogenous TCR promoter and simultaneously knocks out the endogenous TCR). Lentivirally transduced T cells from this additional donor were similarly sorted to yield a 100% 1G4+ population and were similarly co-cultured with the target A375 cancer cell line at an 8; 1 T cell to cancer cell ratio.

In Vivo Mouse Solid Tumour Model

All mouse experiments were completed under a UCSF Institutional Animal Care and Use Committee protocol. 8 to 12 week old NOD/SCID/IL-2Rγ-null (NSG) male mice (Jackson Laboratory) were used for all experiments. Mice were seeded with tumours by subcutaneous injection into a shaved right flank of $1\times10^6$ A375 human melanoma cells (ATCC CRL-1619). At seven days post tumour seeding, tumour size was assessed and mice with tumour volumes between 15-30 $mm^3$ were randomly assigned to experimental and control treatment groups. Indicated numbers of T cells were resuspended in 100 μl of serum-free RPMI and injected retro-orbitally. For tumour sizing experiments, the length and width of the tumour was measured using electronic calipers and volume was calculated as v=1/ 6*π*length*width*(length+width)/2. The investigator was blinded to experimental treatment group during sizing measurements. A bulk edited T cell population ($5\times10^6$) or a sorted NY-ESO-1 TCR+ population ($3\times10^6$) was transferred as indicated in figures and legends. For bulk edited T cell transfers, lentivirally edited cells generally had a higher percentage of NY-ESO-1 positive cells, so mock-infected cells were added to normalize the percentage of total T cells NY-ESO-1+ to equal that of the bulk population of non-virally edited T cells (~10% NY-ESO-1+). For sorted T cell transfers, NY-ESO-1+ T cells were FACS sorted eight days following electroporation, expanded for two additional days, and frozen (Bambanker freezing medium, Bulldog Bio). Non-virally or lentivirally modified human T cells were then thawed and rested in media overnight prior to adoptive transfer. For flow cytometric analysis of adoptively transferred T cells, single-cell suspensions from tumours and spleens were produced by mechanical dissociation of the tissue through a 70 μm filter. All animal experiments were performed in compliance with relevant ethical regulations per an approved IACUC protocol (UCSF), including a tumor size limit of 2.0 cm in any dimension.

In Vivo Functionality of T Cells with Non-Viral TCR Replacement

Figure 7A:
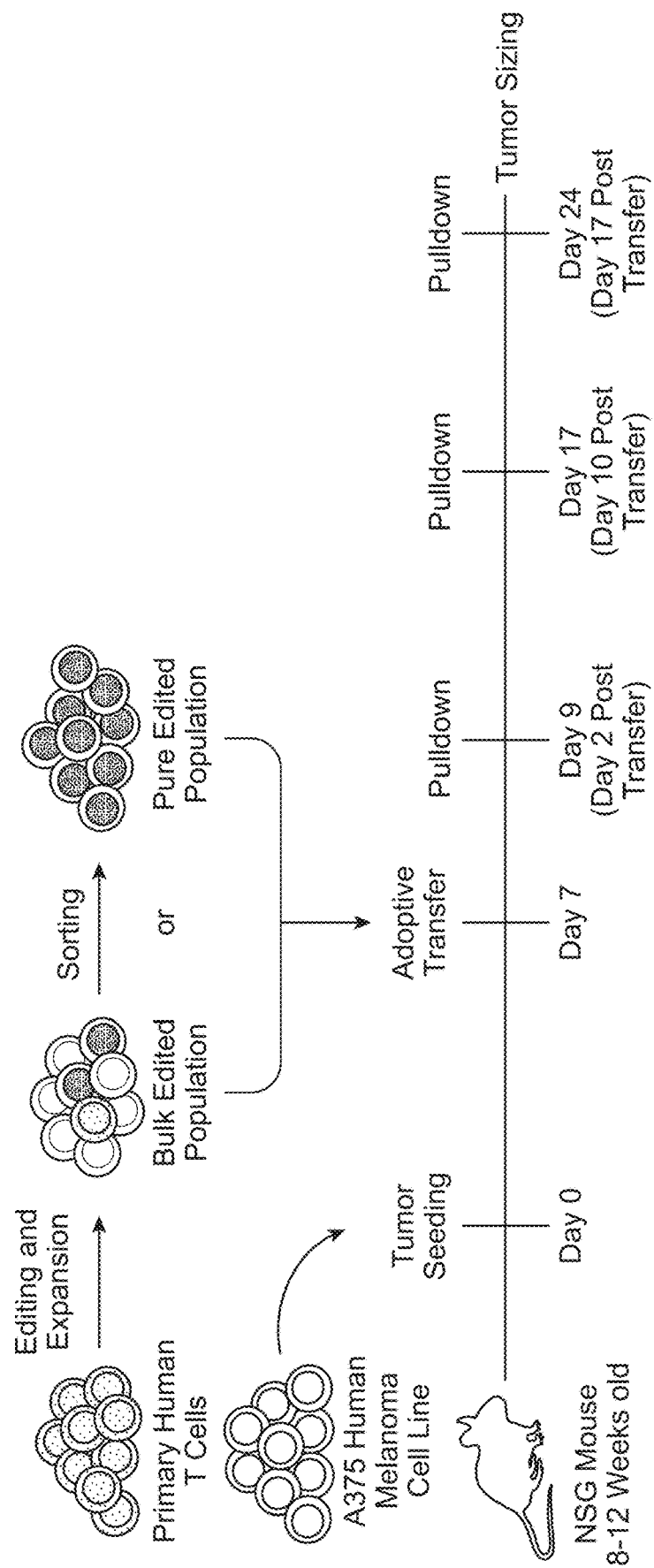
Figure 7F:
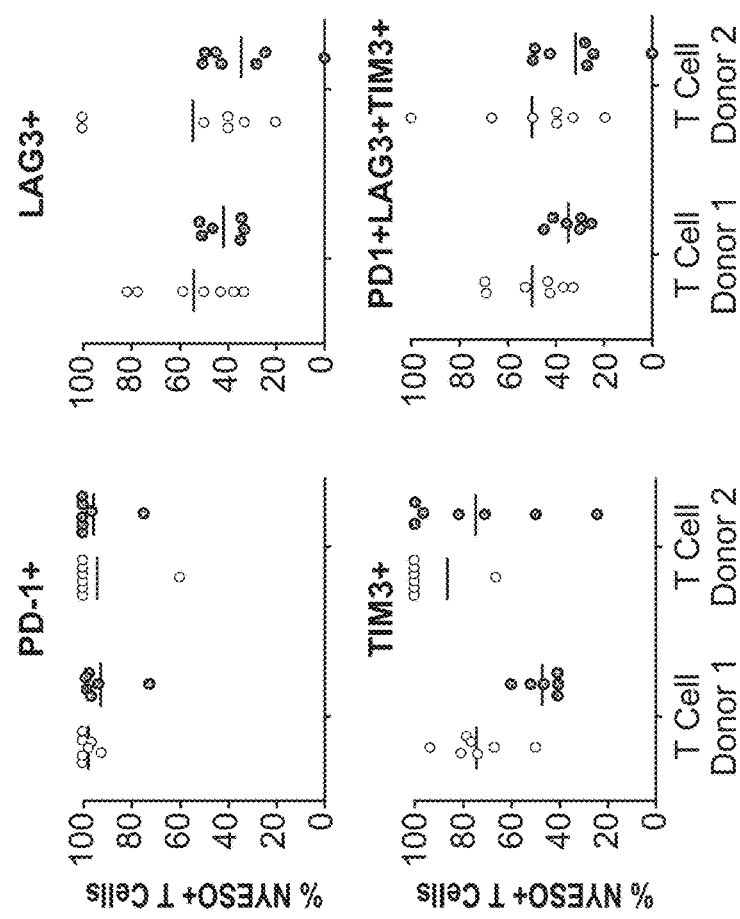
Figure 7E:
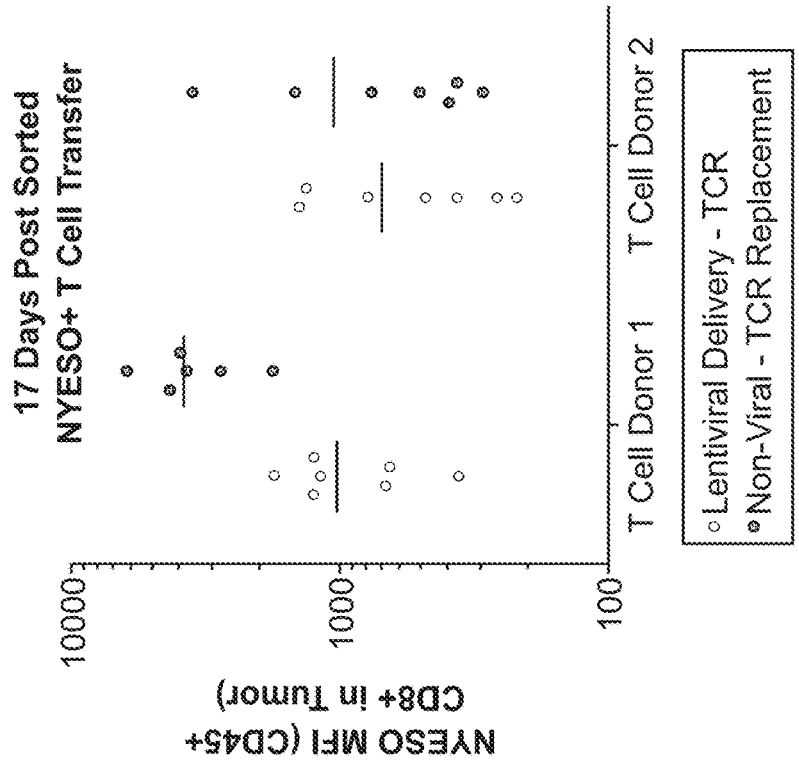

A human antigen specific tumour xenograft model was used (FIG. 7A) to assess in vivo functionality of T cells with a non-viral TCR replacement. 8 to 12 week old NSG mice were seeded with $1\times10^6$ A375 cells (human melanoma cell line; NY-ESO-1 antigen+ and HLA-A*0201+) subcutaneously in a shaved flank. Primary human T cells edited to express an NY-ESO-1 antigen specific TCR were generated (either through lentiviral transduction or non-viral TCR replacement), expanded for 10 days following transduction or electroporation, and frozen. Either a bulk edited population was used (FIGS. 7B-7C) or a NY-ESO-1 TCR+ sorted population (FIGS. 7D-7F) was used. At seven days post tumour seeding, T cells were thawed and adoptively transferred via retro-orbital injection. As shown in FIG. 7B, two days following transfer of 5×10⁶ bulk non-virally targeted T cells (~10% TCR+ NYESO-1+(Red), ~10% TCR+ NYESO-1− (Orange), and ~80% TCR− NYESO-1− (Green), see FIG. 7B), NY-ESO-1+ non-virally edited T cells preferentially accumulated in the tumour vs. the spleen. n=5 mice for each of four human T cell donors. Ten days following transfer of 5×10⁶ bulk non-virally targeted CFSE labeled T cells, NYESO-1 TCR+ cells showed greater proliferation than TCR− or TCR+NYESO-1− T cells, and showed greater proliferation (CFSE Low) in the tumour than in the spleen (FIG. 7C). At ten days post transfer TCR− and TCR+ NYESO− T cells were difficult to find in the tumour (FIG. 7D). FIG. 7D shows longitudinal tumour volume tracks for data summarized in FIG. 8F. 3×10⁶ sorted NY-ESO-1 TCR+ T cells generated either by lentiviral transduction or non-viral TCR replacement were transferred on day 7 post tumour seeding and compared to vehicle only injections until 24 days post tumour seeding. Note that the same data for vehicle control data are shown for each donor in comparison to lentiviral delivery (above) and non-viral TCR replacement (below). In these experiments (FIGS. 7E-7F), seventeen days following T cell transfer, non-virally TCR replaced cells appeared to show greater NY-ESO-1 TCR expression and lower expression of exhaustion markers. Transfer of both lentivirally transduced and non-viral TCR replaced cells showed significant reductions in tumour burden on day 24. In this experimental model, non-viral TCR replacement showed further reductions compared to the lentiviral transduction (FIG. 8F). n=4 (FIG. 7B), n=2 (FIGS. 7D-7F), or n=1 (FIG. 7C) independent healthy donors in 5 (FIGS. 7B-7C) or 7 mice (FIGS. 7D-7F) per donor with mean (FIGS. 7B, 7E, 7F) and standard deviation (FIG. 7B).

Tumour Antigen Specific Function

Figure 8A:
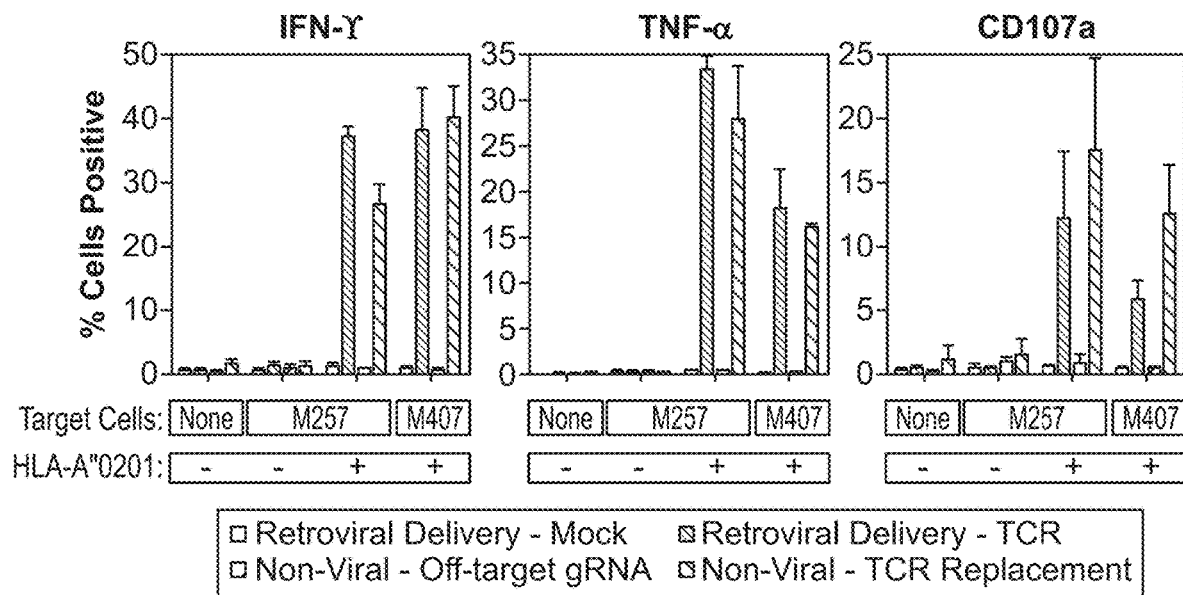
FIG. 8A shows antigen-specific cytokine production and degranulation in CD8+ T cells with a TCR replacement.
Figure 8B:
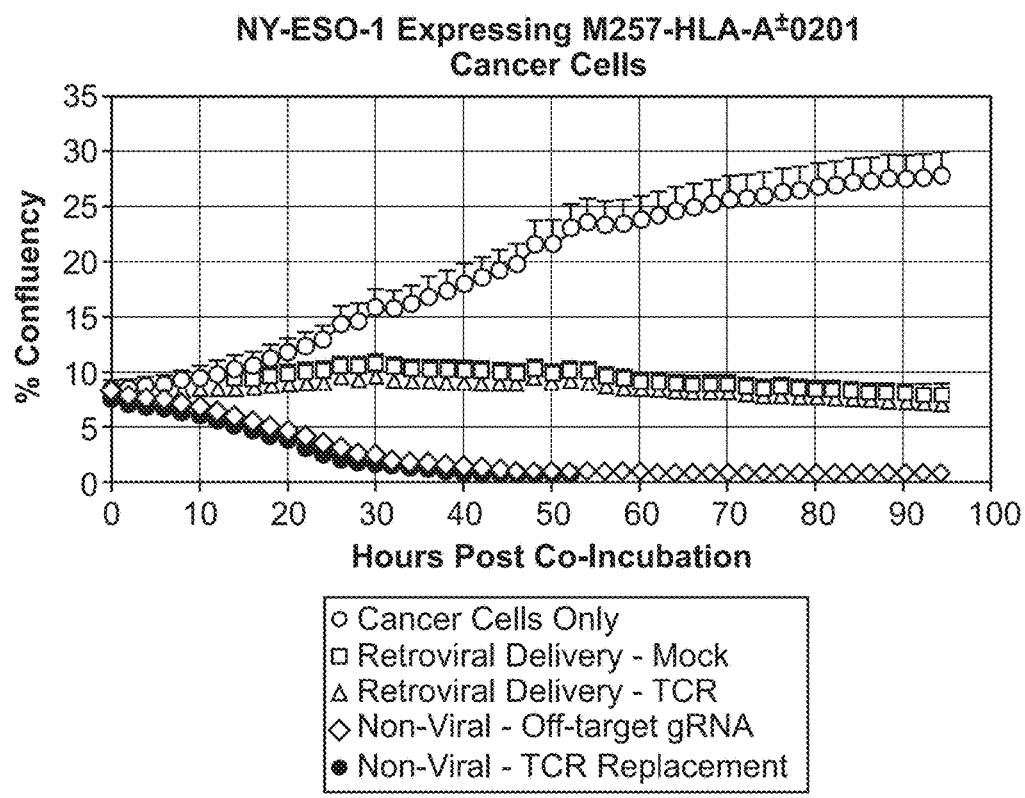
FIG. 8B shows antigen-specific target cell killing by CD8+ T cells with a TCR replacement.
Figure 9D:
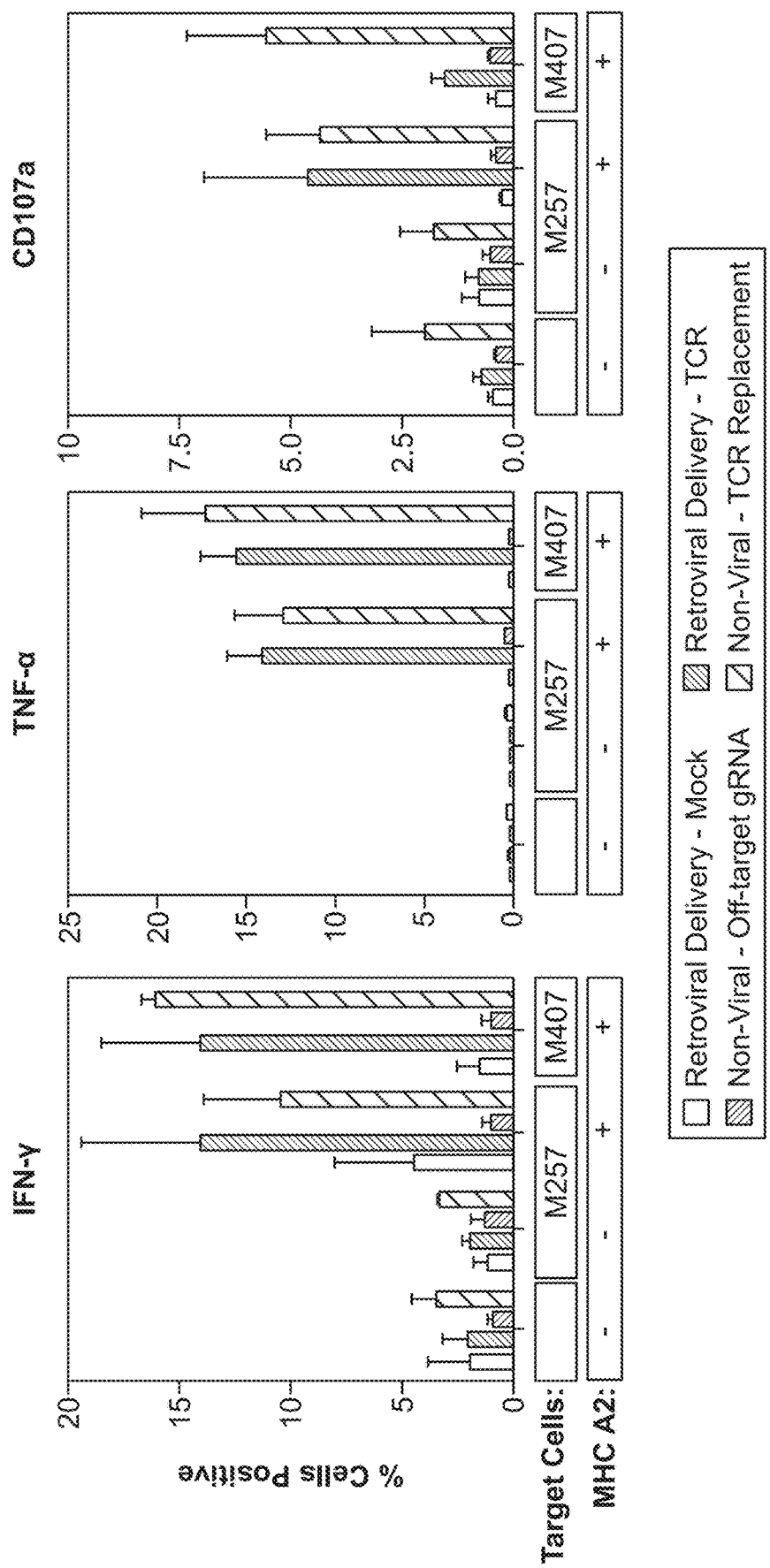
FIG. 9D shows that functional cytokine production was observed selectively following antigen exposure in gated CD4+ T cells, similarly to gated CD8+ T cells (FIG. 8A).
Figure 9E:
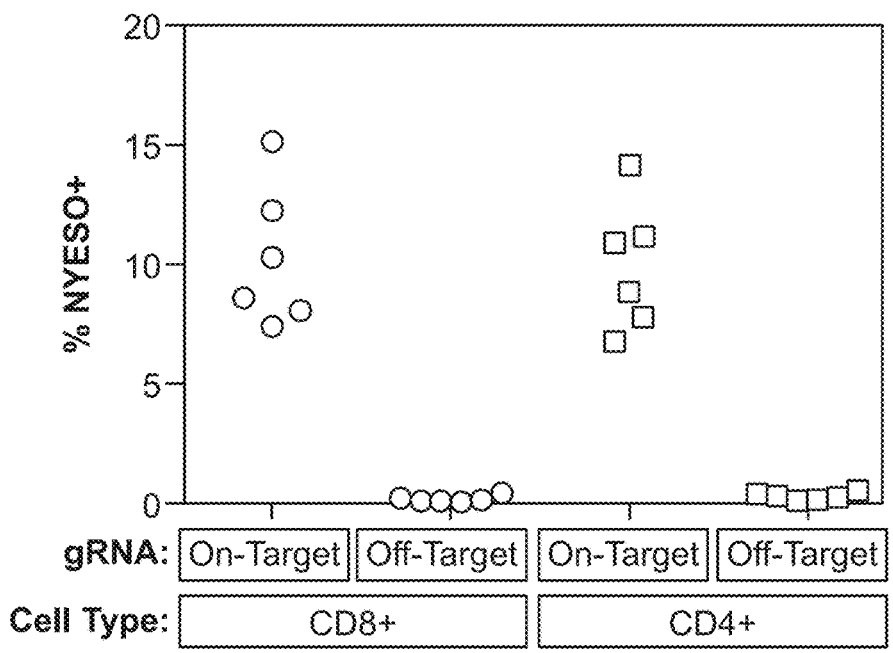
FIG. 9E shows that Non-viral TCR replacement was consistently observed at four days post electroporation in both CD8+ and CD4+ T cells across a cohort of six healthy blood donors.
Figure 9F:
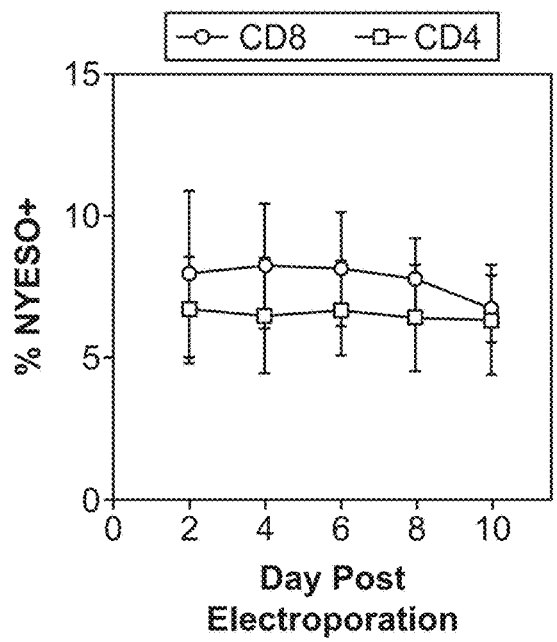
FIG. 9F shows that in a second cohort of six additional healthy blood donors, 100 million T cells from each donor were electroporated with the NY-ESO-1 TCR replacement HDR template and on-target gRNA/Cas9 (FIG. 8D). The percentage of CD4+ and CD8+ T cells that were NY-ESO-1 TCR+ was consistent over ten days of expansion following electroporation.
Figure 9G:
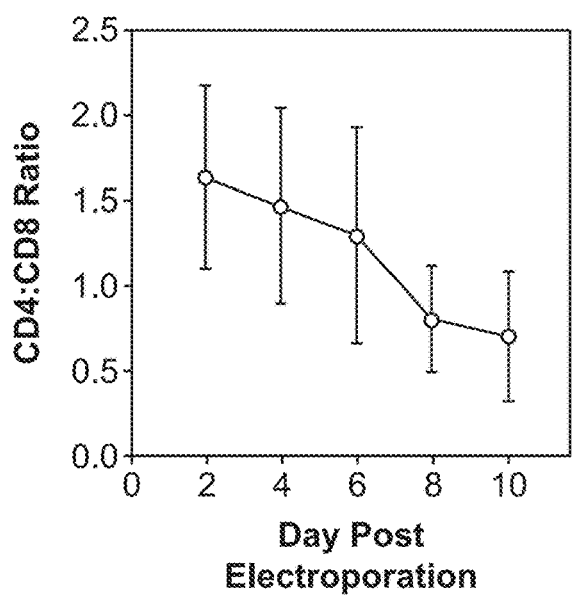
FIG. 9G shows that, over 10 days of expansion following non-viral genome targeting, CD8+ T cells showed a slight proliferative advantage over CD4+ T cells.
Figure 9H:
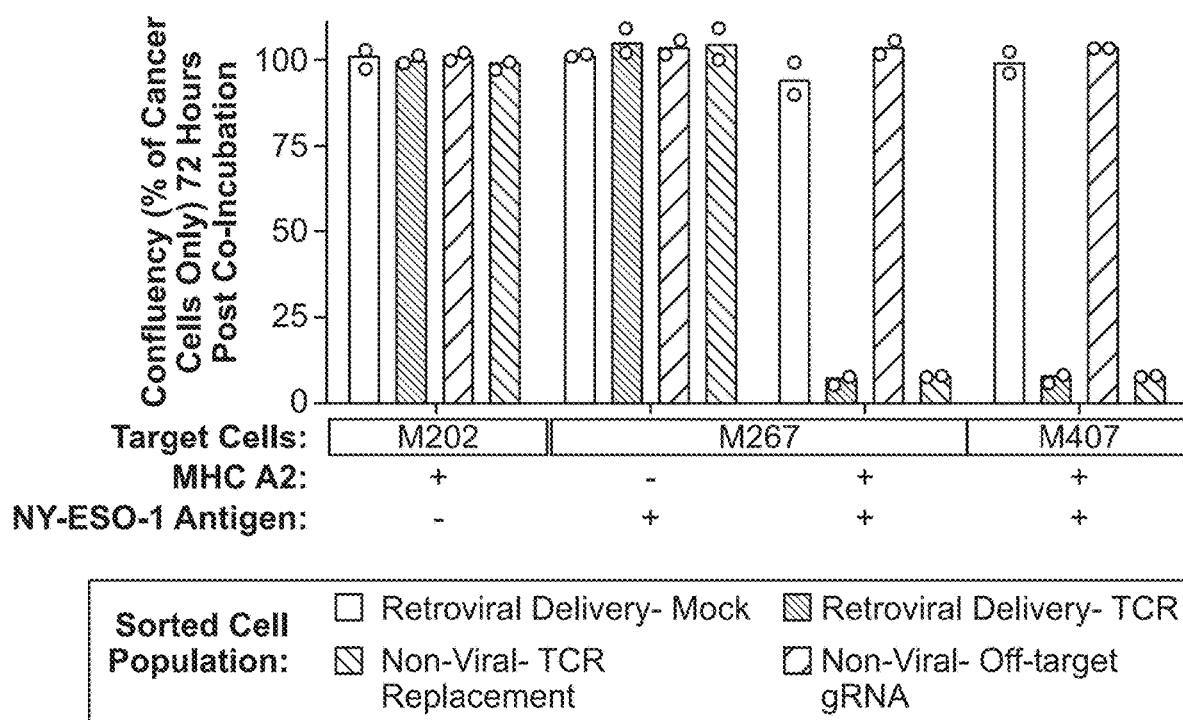
FIG. 9H shows the results of co-incubation of the indicated melanoma cell lines with the indicated sorted T cell populations at a ratio of 1:5 T cells to cancer cells. At 72 hours post co-incubation the percent cancer cell confluency was recorded with by automated microscopy (where nuclear RFP marks the cancer cells). T Cells expressing the NY-ESO-1 antigen specific TCR, either by retroviral transduction or by non-viral knock-in endogenous TCR replacement both showed robust target cell killing only in the target cancer cell lines expressing both NY-ESO-1 and the HLA-A*0201 class I MHC allele.
Figure 9I:
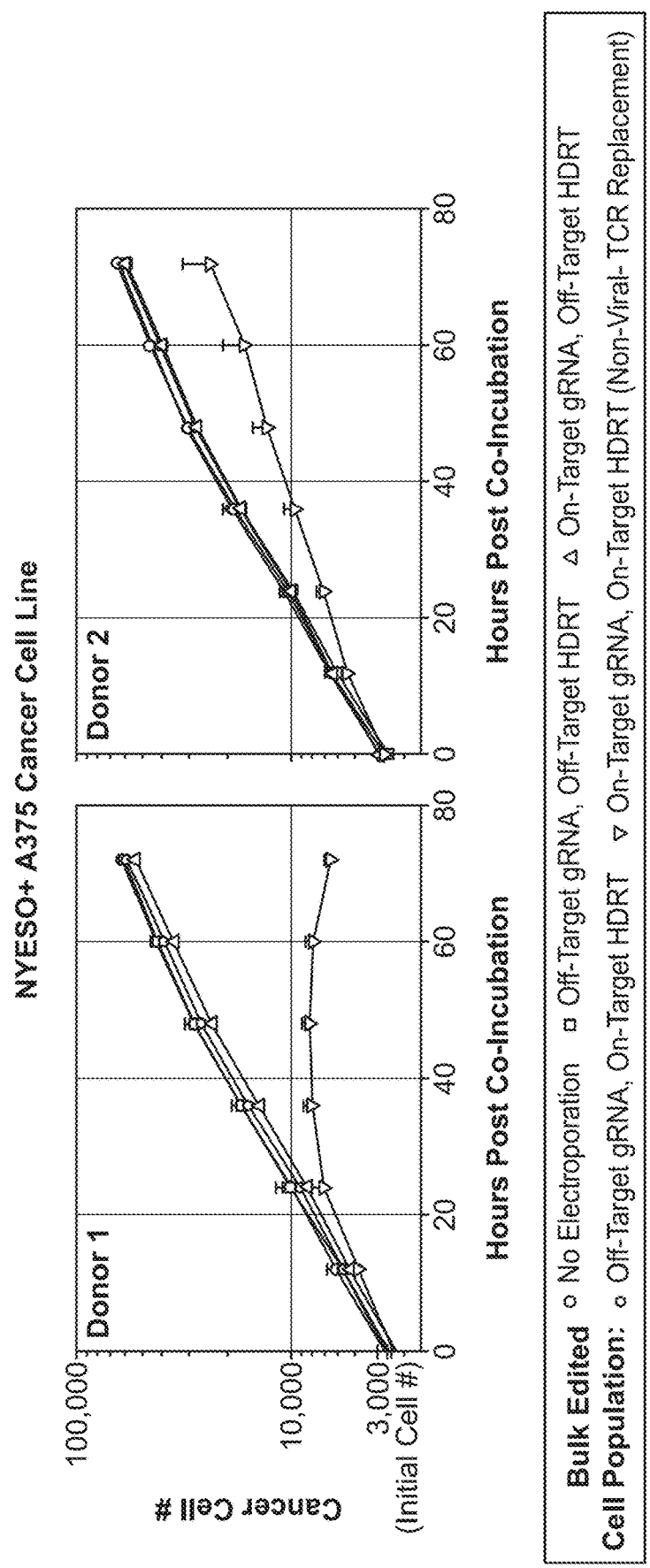
FIG. 9I shows the results of using a matrix of on/off target gRNAs and on/off target HDR templates for target cell killing of the NY-ESO-1+HLA-A*0201+A375 cancer cell line (off-target gRNA and HDRT were specific for RAB11A-GFP fusion protein knock-in). Only cells with both the on-target gRNA as well as the on-target HDR template demonstrated target cell killing.
Figure 9J:
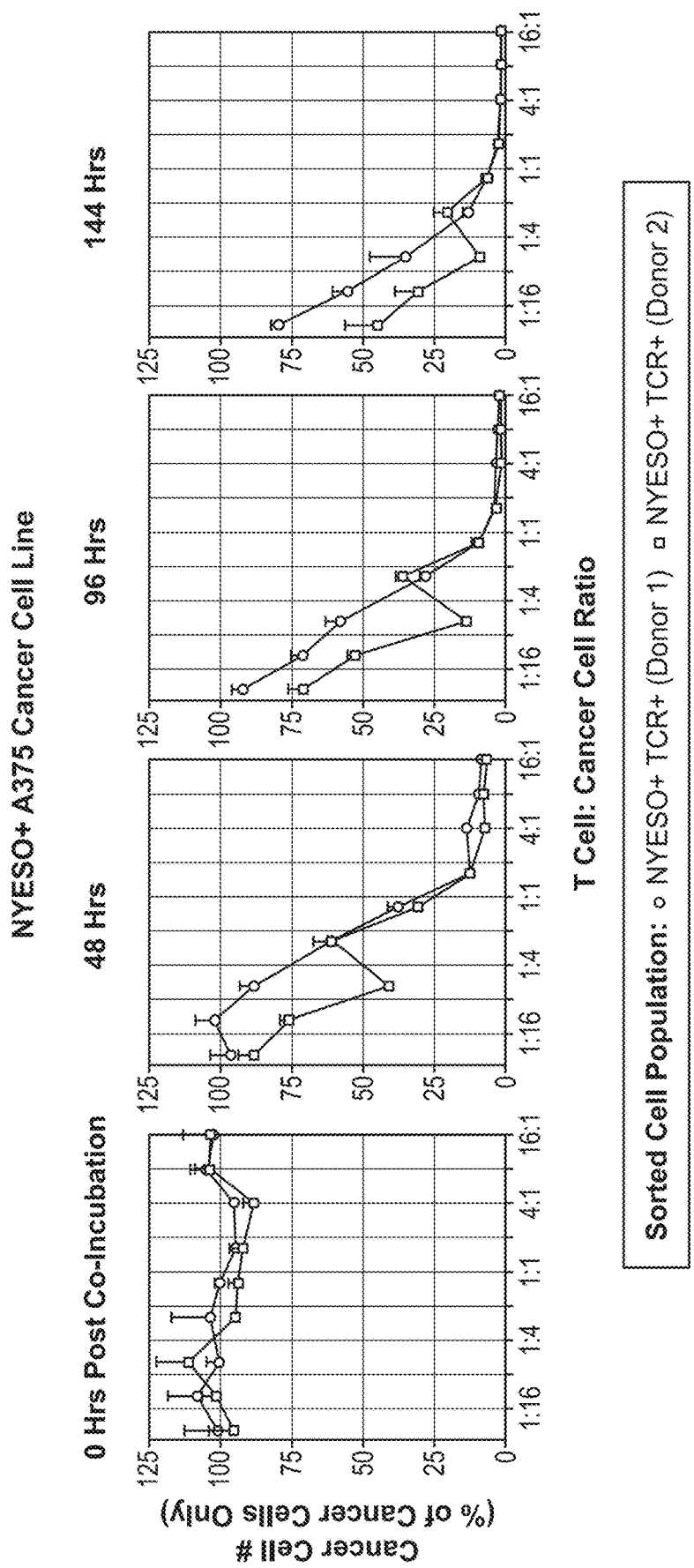
FIG. 9J shows that sorted NY-ESO-1+ TCR+ cells from a bulk T cell edited population (on-target gRNA, on-target HDR template) showed a strong dose-response effect for target cancer cell killing. Within 48 hours T cell to cancer cell ratios of 2:1 and greater showed almost complete killing of the target cancer cells. By 144 hours, T cell to cancer cell ratios of less than 1:16 showed evidence of robust target cell killing.
Figure 9K:
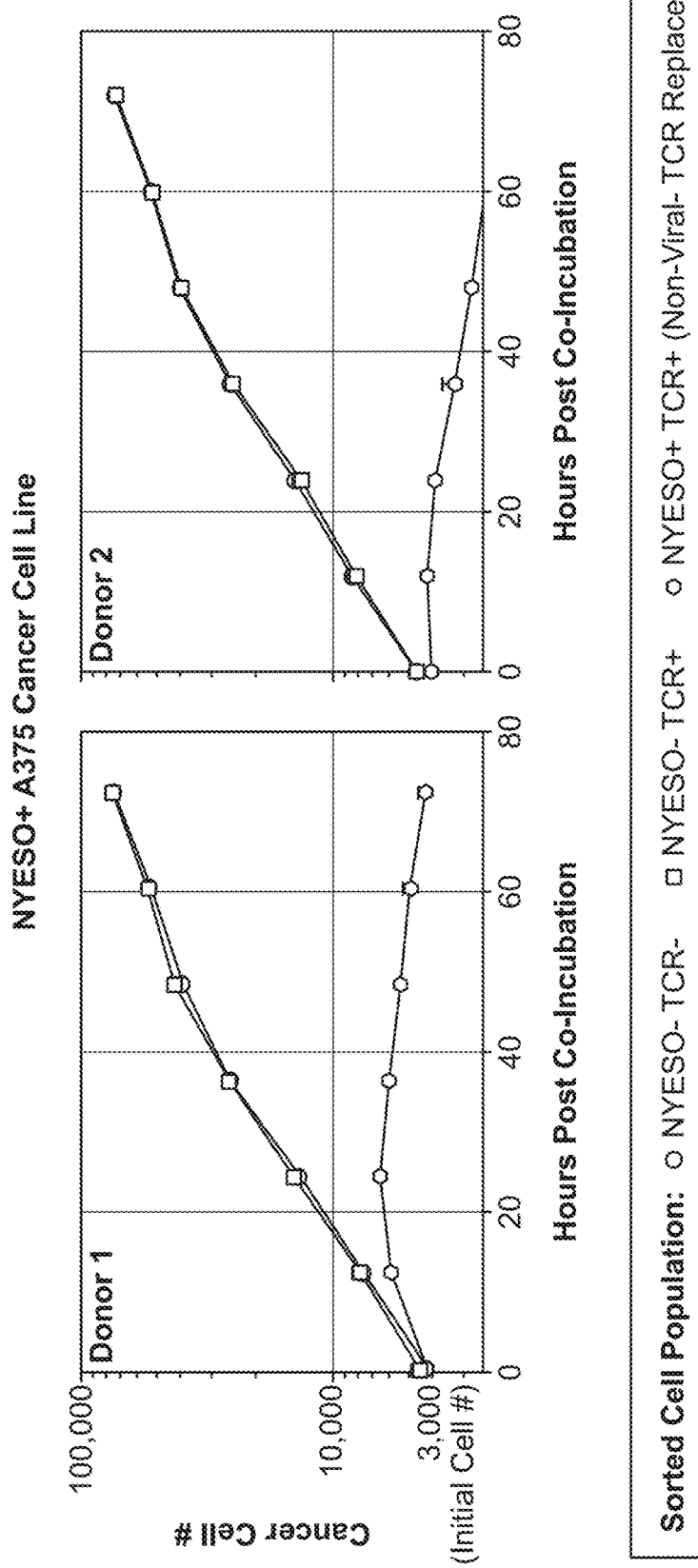
FIG. 9K shows that target cell killing by non-viral TCR replacement T cells was due specifically to the NY-ESO-1-recognizing TCR+ cell population observed by flow cytometry after non-viral TCR replacement. Starting with the bulk edited T cell population (all of which had been electroporated with the on-target gRNA and HDR template), we separately sorted three populations of cells: the NY-ESO-1+TCR+ cells (non-virally replaced TCR), the NY-ESO-1-TCR− cells (TCR knockout) (grey), and the NY-ESO-1-TCR+ cells (those that retained their native TCR but did not have the NY-ESO specific knock-in TCR). Only the sorted NY-ESO-1+ TCR+ population demonstrated target cell killing (4:1 T cell to cancer cell ratio). One representative donor from n=2 (a,d) or n=3 (b,c) independent healthy donors with mean and standard deviation of technical triplicates (d). Mean and standard deviations of n=6 independent healthy donors (e,f) or of four technical replicates for n=2 independent healthy donors (i-k) are shown. Mean and individual values for n=2 independent healthy donors (h).

The tumour antigen-specific function of targeted human T cells was also assessed. When the targeted T cells were co-cultured with two different NY-ESO-1+ melanoma cell lines, M257 and M407, the modified T cells robustly and specifically produced IFN-γ and TNF-α and induced T cell degranulation (measured by CD107a surface expression) (FIG. 8A). Cytokine production and degranulation only occurred when the NY-ESO-1 TCR T cells were exposed to cell lines expressing the appropriate HLA-A*0201 class I MEW allele required to present the cognate NY-ESO-1 peptide. Both the CD8+ and CD4+ T cell response was consistent across healthy donors, and was comparable to the response of T cells from the same healthy donor in which the NY-ESO-1 TCR was transduced by gamma retrovirus and heterologously expressed using a viral promoter (FIG. 8A and FIG. 9D). NY-ESO-1 TCR knock-in T cells rapidly killed target M257-HLA-A*0201 cancer cells in vitro at rates similar to the positive control, retrovirally transduced T cells (FIG. 8B). Killing was selective for target cells expressing NY-ESO-1 antigen and the HLA-A*0201 allele, consistent across donors, and depended on the T cells being modified using both the correct gRNA and HDR template (FIGS. 9H-9K).

Figure 8C:
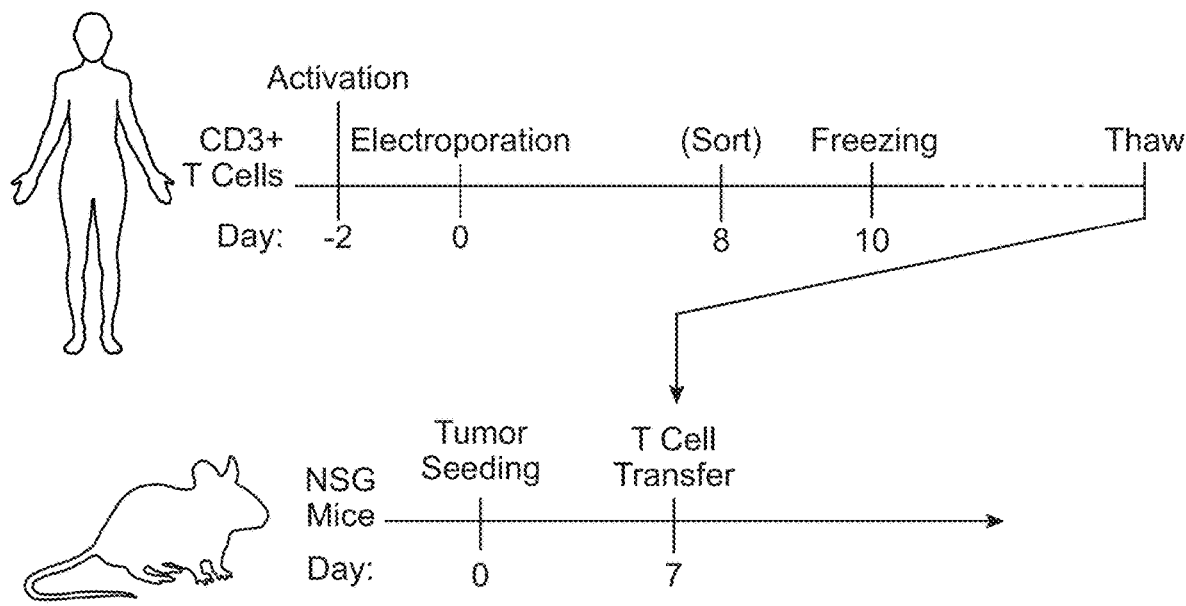
FIG. 8C is a schematic of a tumour mouse xenograft model.
Figure 8D:
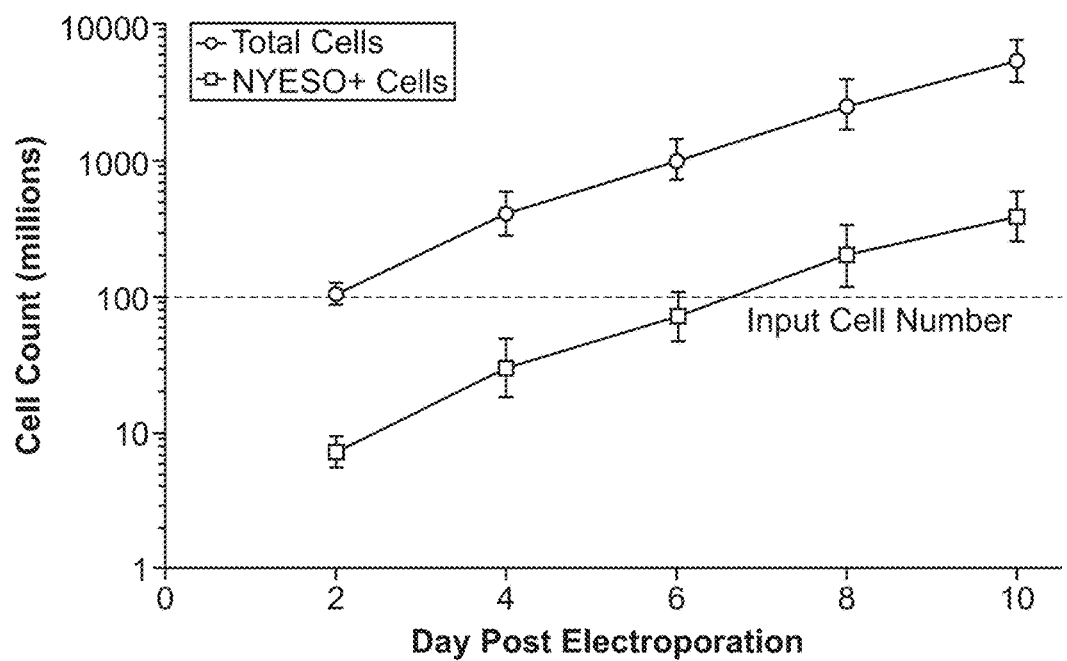
FIG. 8D shows the scalability of non-viral replacement of the endogenous TCR for adoptive cell therapy.
Figure 8E:
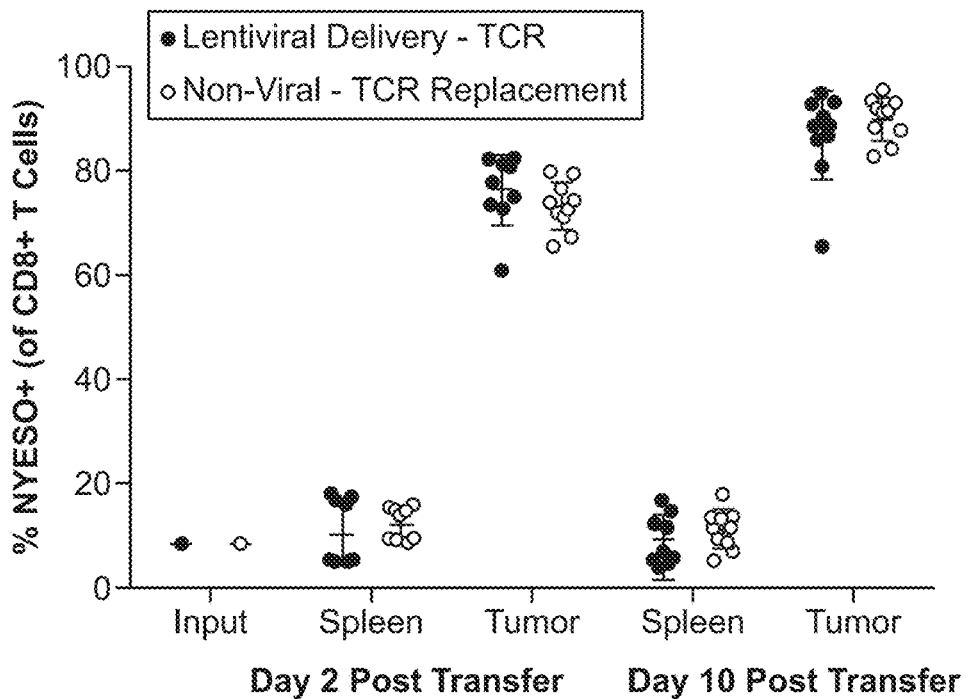
FIG. 8E shows preferential in vivo localization of NY-ESO-1 TCR+ T cells to a tumour.
Figure 8F:
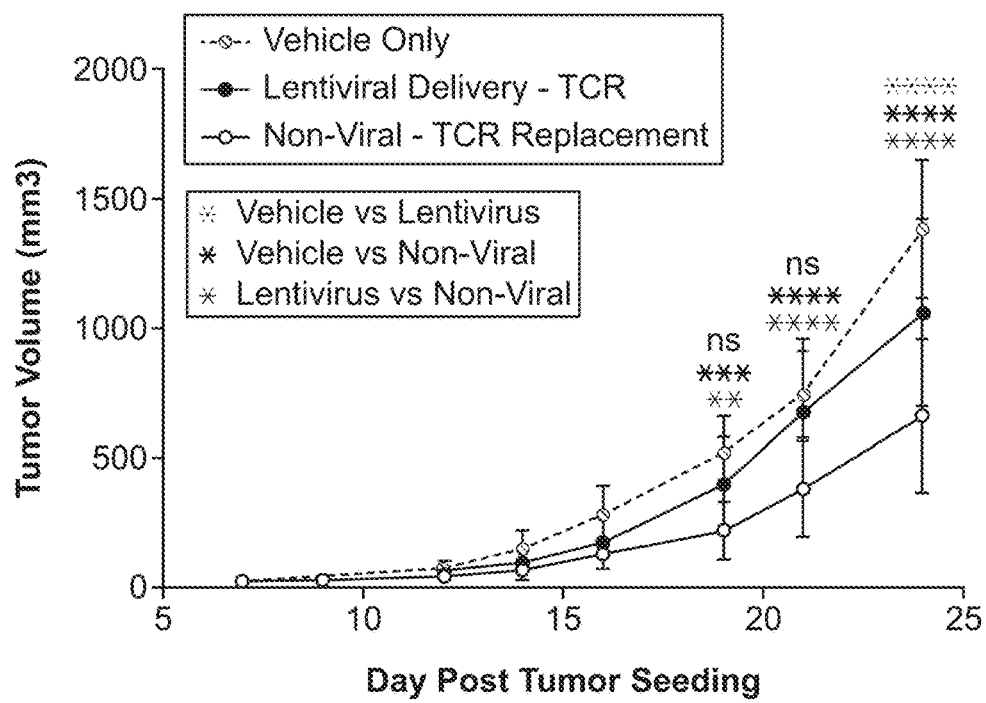
FIG. 8F shows tumour growth following adoptive transfer of NY-ESO-1 TCR+non-virally or lentivirally modified or vehicle alone (saline). n=2 (a,b) independent healthy donors with mean and standard deviation of technical triplicates (a,b). n=6 (d) or n=2 (e,f) independent healthy donors in 5 (e) or 7 mice (f) with mean and standard deviation (d-f). P<0.01, *P<0.001, ****P<0.0001 (Two Way ANOVA with Holm-Sidak's multiple comparisons test).

Finally, it was confirmed that non-viral genome targeting could be used to generate NY-ESO-1 TCR cells at scale and that these cells have in vivo anti-tumour function (FIG. 8C and FIG. 7A). Given that knock-in efficiency was lower with non-viral targeting than with comparable sized AAV templates, whether sufficient numbers of NY-ESO-1 positive cells for adoptive cell therapies was ensured. 100 million T cells from six healthy donors, which after ten days of expansion yielded an average of 385 million NY-ESO-1 TCR T cells per donor (FIG. 8D). NY-ESO-1 TCR knock-in T cells preferentially localized to, persisted at, and proliferated in the tumour rather than the spleen, similar to positive control lentivirally-transduced T cells (FIG. 8E and FIGS. 7B-7F). Adoptive transfer of sorted NY-ESO-1 TCR T cells also reduced the tumour burden in treated animals (FIG. 8F).

What is claimed is:

1. A modified primary human T cell comprising: at least one nucleic acid sequence comprising at least one heterologous gene non-virally inserted into one or both of:
   an endogenous T cell receptor alpha subunit constant gene (TRAC); and
   an endogenous T cell receptor beta subunit constant gene (TRBC), wherein the at least one heterologous gene encodes at least one antigen-specific receptor that specifically binds the target antigen expressed by a cancer, and wherein the at least one nucleic acid sequence is at least 500 bp in size.

2. The T cell of claim 1, wherein the modified human T cell does not comprise a viral vector.

3. The T cell of claim 1, wherein the at least one nucleic acid sequence is at least 1.5 kb in size.

4. The T cell of claim 1, wherein the at least one nucleic acid sequence is non-virally inserted into an exon of the T cell receptor alpha subunit constant gene (TRAC) or into an exon of the T cell receptor beta subunit constant gene (TRBC).

5. The T cell of claim 1, wherein the at least one heterologous gene comprises at least one of:
   (a) a variable region of a heterologous T cell receptor alpha (TCR-α) chain and
   (b) a variable region of a heterologous T cell receptor beta (TCR-β) chain.

6. The T cell of claim 1, wherein the at least one heterologous gene comprises at least one of:
   (1) a) a variable region of a heterologous T cell receptor alpha (TCR-α) chain or b) a variable region and constant region of the heterologous TCR-α chain; and
   (2) a) a variable region of a heterologous T cell receptor beta (TCR-β) chain or b) a variable region and constant region of the heterologous TCR-β chain.

7. The T cell of claim 6, wherein the at least one heterologous gene comprises each of:
   (1) the a) variable region of the heterologous TCR-α chain or b) variable region and constant region of the heterologous TCR-α chain; and
   (2) the a) variable region of the heterologous TCR-β chain or b) variable region and constant region of the heterologous TCR-β chain.

8. The T cell of claim 7, wherein one or more coding sequences for the heterologous TCR-α chain and the heterologous TCR-β chain are linked by a linker sequence or a multicistronic element.

9. The T cell of claim 8, wherein the linker sequence is a cleavable linker sequence that is cleaved to generate the heterologous TCR-α chain gene and the heterologous TCR-β chain gene.

10. The T cell of claim 8, wherein the heterologous gene encodes the TCR-α chain and the heterologous TCR-β chain and wherein the heterologous gene is inserted into TRAC.

11. The T cell of claim 1, wherein the at least one heterologous gene is non-virally inserted into an endogenous TRAC, wherein the at least one heterologous gene comprises each of:

(1) a) a variable region of the heterologous TCR-α chain or b) a variable region and constant region of the heterologous TCR-α chain; and
(2) a) a variable region of the heterologous TCR-β chain or b) a variable region and constant region of the heterologous TCR-β chain, wherein the heterologous TCR-α chain and the heterologous TCR-β chain are operably linked by a cleavable linker sequence that is cleaved to generate the heterologous TCR-α chain and the heterologous TCR-β chain, and wherein the heterologous TCR-α chain and the heterologous TCR-β form an antigen-specific T cell receptor (TCR) that recognizes the target antigen expressed by the cancer.

12. The T cell of claim 1, wherein expression of the at least one heterologous gene is under the control of an endogenous promoter.

13. The T cell of claim 1, wherein the modified human T cell is a CD8+ T cell or a CD4+ T cell.

14. The T cell of claim 13, wherein the CD8+ T cell or CD4+ T cell is an effector T cell or a naïve T cell.

15. The T cell of claim 1, wherein the primary human T cell is obtained from a subject having cancer and modified to comprise the at least one nucleic acid sequence comprising at least one heterologous gene.

16. A population of cells comprising a plurality of the primary human T cell of claim 1.

* * * * *